United States Patent [19]

Hastings

[11] Patent Number: 5,346,508
[45] Date of Patent: Sep. 13, 1994

[54] APPARATUS AND METHOD FOR PERFORMING DIAGNOSTICS AND INTRAVASCULAR THERAPIES

[75] Inventor: Roger Hastings, Burnsville, Minn.

[73] Assignee: SCIMED Life Systems, Inc., Maple Grove, Minn.

[21] Appl. No.: 55,702

[22] Filed: Apr. 29, 1993

[51] Int. Cl.$^5$ .............................................. A61B 5/026
[52] U.S. Cl. ...................................... 607/99; 128/692
[58] Field of Search ............................ 128/691–692, 128/713; 607/89, 99, 100; 606/7, 27–31, 41–42, 192, 194; 604/96

[56] References Cited

U.S. PATENT DOCUMENTS

| | | |
|---|---|---|
| 3,352,154 | 11/1967 | Djorup . |
| 3,438,253 | 4/1969 | Kuether et al. . |
| 3,789,831 | 2/1974 | Kopaniky et al. ............... 128/692 |
| 4,059,982 | 11/1977 | Bowman ..................... 128/691 X |
| 4,799,479 | 1/1989 | Spears . |
| 4,920,967 | 5/1990 | Cottonaro et al. . |
| 4,961,433 | 10/1990 | Christian . |
| 5,035,694 | 7/1991 | Kasprzyk et al. . |
| 5,041,089 | 8/1991 | Mueller et al. . |
| 5,078,717 | 1/1992 | Parins et al. . |
| 5,094,246 | 3/1992 | Rusz et al. . |
| 5,114,423 | 5/1992 | Kasprzyk et al. . |
| 5,184,621 | 2/1993 | Vogel et al. . |
| 5,190,540 | 3/1993 | Lee .......................... 606/28 |

FOREIGN PATENT DOCUMENTS

WO91/03207 3/1991 PCT Int'l Appl. .
WO92/00710 1/1992 PCT Int'l Appl. .
WO92/22240 12/1992 PCT Int'l Appl. .

OTHER PUBLICATIONS

Article: "Advantage of Peak Velocity Over Mean Velocity Measurements Made by Doppler Catheters", Scott J. Denardo et al., University of California, San Francisco, Calif. Supplement I Circulation vol. 26, No. 4, Oct. 1992, p. I-870.
Brochure "Cardiometrics® Flowire®/FloMap® Report," Jan. 1992, 4 pages.
Brochure, "Cardiometrics®" date unknown, 2 pages.

Primary Examiner—Angela D. Sykes
Attorney, Agent, or Firm—Merchant, Gould, Smith, Edell, Welter & Schmidt

[57] ABSTRACT

An apparatus and method for performing diagnostics and intravascular therapies. A guidewire anemometer can be used to measure the velocity of fluid flowing through the vasculature. An in-line anemometer can be used to measure the volumetric flow rate of fluid transported out of a patient's body. A heated balloon catheter can be used to deliver heat therapy no a vessel wall in a patient's vasculature.

15 Claims, 18 Drawing Sheets

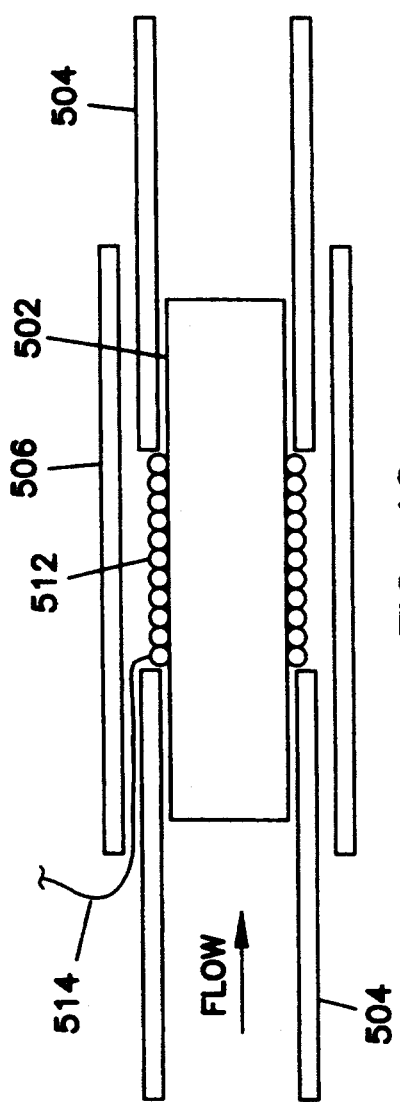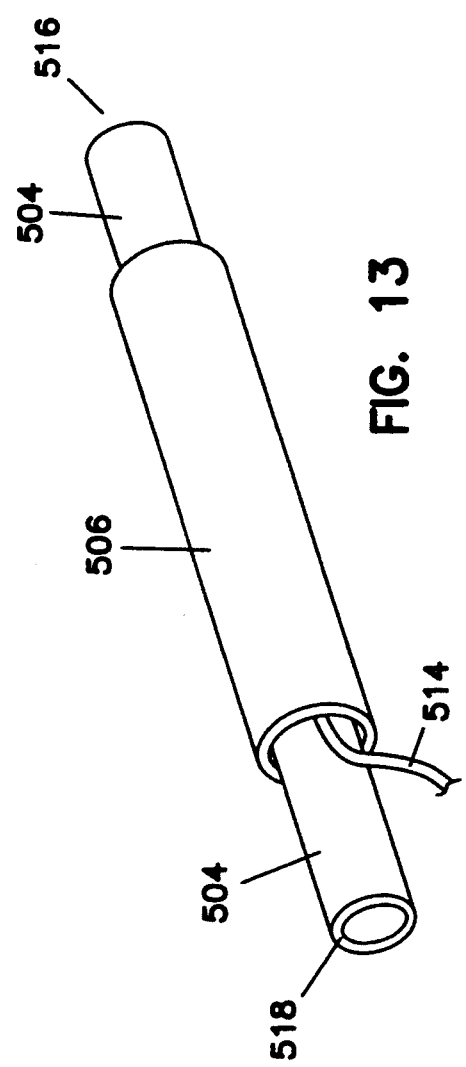

APPARATUS AND METHOD FOR PERFORMING DIAGNOSTICS AND INTRAVASCULAR THERAPIES

BACKGROUND OF THE INVENTION

Various apparatus and methods have been designed to perform therapy and/or diagnostics in the vascular system. In the area of intravascular therapy, heated balloon dilation catheters have been used to deliver heat to the vessel wall. Some of these catheters heat the inflation fluid within the balloon by means of a heating element such as a coil wrapped around the catheter body under the balloon region. The power delivered to the heating element may be controlled by a conventional analog feedback circuit which has one or more temperature sensing devices such as a thermocouple or thermistor secured to the inner surface of the balloon or to the heating element.

Several disadvantages may be associated with such catheters. Because independent sensors are used to detect the temperature of either the heating elements, inflation fluid or balloon surface inaccuracies may result due to defects in the sensor or a limited range of accuracy. In addition, the position of the sensor may lead to inaccuracies. For example, a sensor placed on the balloon surface does not necessarily measure the hottest point on the catheter. This arises because the balloon surface is not heated directly and thus its temperature lags behind the temperature of the inflation fluid. Once the sensor detects that the temperature at a given point on the balloon surface has reached a maximum permissible value, the temperature of other points on the balloon surface may have increased beyond that value due to the higher temperature of the inflation fluid within the balloon. In addition, the temperature of the surface of the balloon is related to the thermal diffusivity of the adjacent tissues. Thus, the temperature at various points along the balloon surface may be different. The sensor detects the temperature at a given point on the surface while the temperature at other points may be higher. This may cause the temperature of the balloon surface to reach a level which could damage the vessel in which the catheter is placed. In addition, the low profile of the catheter may be compromised by the inclusion of a sensor or sensors on the catheter.

Other catheters directly heat the balloon surface itself. For example, U.S. Pat. No. 5,035,694 (Kasprzyk et al.) discloses a catheter having a conductive layer 52 formed on the inside of the balloon. (See FIG. 4). The layer is heated by making contact with conductors 50 and 51 so that the exterior working surface temperature of the balloon is raised. The power supplied to the conductors may be controlled in response to the temperature of the balloon by a suitable feedback control system. (See FIG. 1). The control circuit includes an ohmmeter 34 used to monitor the resistive load of the balloon and control the output of the power source in response thereto. The output of the ohmmeter is compared with a signal representing a desired set point in a controller 35 and fed back to control the power source.

Several disadvantages may be associated with such a catheter. Stresses may be placed on the conductive layer as the balloon is inflated and deflated. This may cause the conductive layer no crack or tear. Also, the properties of the conductive layer may change over a period of time and use thereby leading to results which may not be stable and repeatable over a period of time.

In the area of intravascular diagnostics, various apparatus and methods have been used to measure the flow of blood through a vessel. For example, U.S. Pat. No. 4,920,967 (Cottonaro et al.) discloses a wire guide provided with a Doppler mechanism for determining the blood flow velocity in the region of the distal end of the wire guide. A pulsed Doppler angioplasty guidewire is available commercially from Cardiometrics of Mountain View, Calif. under the trade name FLOWIRE ®.

Several disadvantages may be associated with such Doppler guidewires. Using Doppler technology allows such guidewires to measure the peak-to-peak velocity and not necessarily a true mean velocity. (S. Denardo et al., "Advantages of Peak Velocity Over Mean Velocity Measurements Made by Doppler Catheters," *Circulation*, Vol. 86, No. 4, Supplement I, I-870, October 1992). In addition, such guidewires measure the component of velocity along the sensor axis and thus the measurements made using such systems are dependent upon the angle of the sensor with reference to the vessel.

Other devices not limited to the field of intravascular diagnostics utilize a heated wire to determine characteristics such as the velocity of a flowing fluid. This is commonly referred to as "hot-wire" anemometry. A wire having a resistance proportional to its temperature is heated to a select temperature above the ambient temperature of the fluid in which it is placed. As the cooler fluid flows past the wire, variations are caused in the temperature of the wire and thus its resistance. The resistance of the wire is used to control its temperature through the use of a bridge circuit in which the wire forms one arm of the bridge. As the resistance of the wire changes the balance of the bridge is upset. The temperature of the wire and thus its resistance is increased by increasing the current delivered to the bridge to restore balance. The change in current delivered to the bridge circuit is measured and reflects the velocity of the flowing fluid. Examples of such systems can be found in U.S. Pat. Nos. 3,352,154 (Djorup); 3,438,253 (Kuether et al.) and 5,094,246 (Rusz et al.)

Several disadvantages may be associated with such anemometers that utilize bridge circuits as described above. To provide accurate results, precision power resistors may be required. In addition, in order to vary the temperature at which the wire is to be maintained, a precision power potentiometer may also be required. Use of such power resistors and potentiometers increase the cost associated with such anemometers. In addition, a large power supply may be required because equal current has to be supplied to both arms of the bridge. Using a bridge circuit to provide control thus results in a bulky system with limited accuracy.

It is desirable to provide an apparatus and method for performing intravascular therapy and diagnostics which does not suffer from the disadvantages listed above.

SUMMARY OF THE INVENTION

According to one aspect of the present invention, an apparatus and method are provided for performing intravascular therapy using a dilation catheter having a heating element located in the interior of the balloon. A variable driving signal is generated and applied to the heating element to heat the inflation fluid within the balloon. A current meter and voltage meter measure the current through and the voltage across the heating element respectively. A divider circuit communicates with the current and voltage meters to derive a measured signal. A subtractor circuit compares the measured signal with a desired signal and generates an output signal representative of the comparison. A feed back circuit receives the output signal from the subtractor circuit and generates an output signal having an exponential relation to the output of the subtractor circuit. The output of the feedback circuit communicates with the signal source to vary the driving signal delivered to the heating element.

According to another aspect of the present invention, an intravascular guidewire anemometer is provided having a guidewire with a proximal and distal end and a heating element located near the distal end of the guidewire.

According to still another aspect of the present invention an apparatus and method are provided for performing intravascular diagnostics using a guidewire anemometer as described above. More particularly, the heating element is heated to a select temperature by a variable driving signal. The anemometer is exposed to cooler flowing fluid and the power delivered to the heating element needed to maintain its temperature at the select temperature is measured. From this measurement is derived the velocity of the flowing fluid.

According to still another aspect of the present invention, an in-line anemometer is provided for measuring volumetric flow of a flowing fluid. The anemometer includes an inner tubular member defining an inner lumen with a heating element positioned on the exterior of the inner tubular member. An intermediate member formed by two side tubes are placed concentrically over an end portion of the inner tubular member, the two side tubes being separated by the heating element. An outer tubular member is concentrically disposed over the heating element and a portion of the side tubes.

According to still another aspect of the present invention, an apparatus and method are provided for performing non-intravascular diagnostics using an in-line anemometer as previously described. More particularly, the heating element is heated to a select temperature. As cooler fluid flows through the inner lumen the power needed to maintain the heating element at the select temperature is measured. Derived from this measurement is a volumetric flow rate of the fluid flowing through the inner lumen.

BRIEF DESCRIPTION OF THE DRAWINGS

FIG. 5 is a detailed schematic of a portion of the apparatus shown in FIG. 3a.

FIG. 12 illustrates a cross-sectional view of an in-line anemometer usable with the apparatus of FIG. 1 according to a third preferred embodiment of the present invention.

FIG. 13 is a schematic view of the in-line anemometer of FIG. 12.

DETAILED DESCRIPTION OF THE PRESENTLY PREFERRED EMBODIMENTS

Figure 1:
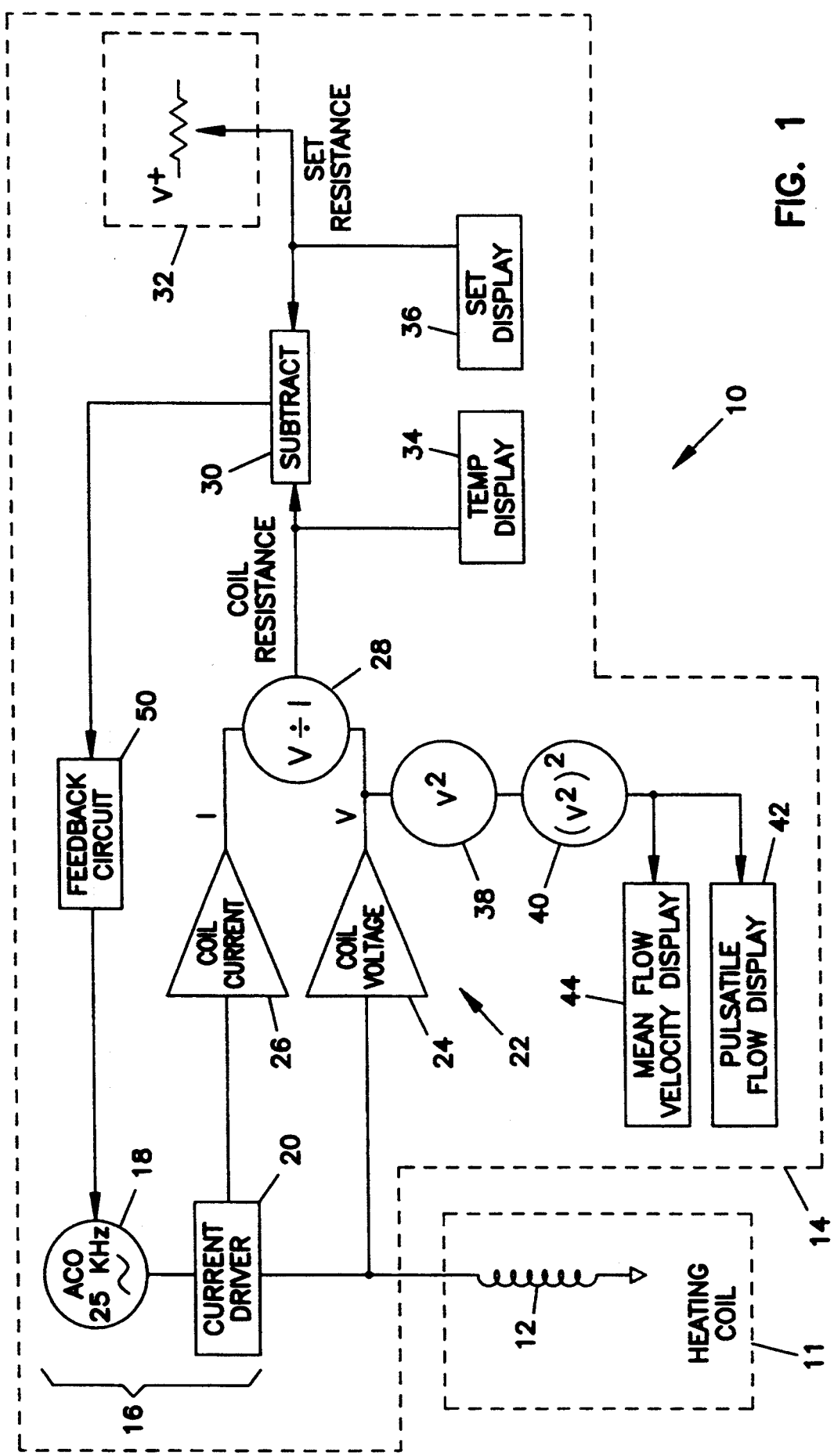
FIG. 1 illustrates a simplified block schematic of an apparatus for performing intravascular therapy and diagnostics according to a preferred embodiment of the present invention.

FIG. 1 illustrates a simplified block schematic of an apparatus 10 for performing intravascular therapy and diagnostics according to a preferred embodiment of the present inventions. Apparatus 10 includes a heating element in the form of a coil 12 located in a device 11 and circuitry 14. Various embodiments of device 11 will be described with reference to FIGS. 9–12. The device 11 in which the coil 12 is embodied is not limited to intravascular use as will be described with reference to FIGS. 11 and 12.

In general a controlled signal source 16 preferably formed by an amplitude controlled oscillator 18 and a current driver 20 delivers current to the coil 12. The resistance of the coil 12 is measured by a meter 22 preferably including a current meter 24, a voltage meter 26 and a precision divider circuit 28. Due to characteristics of the coil 12 which will be described later, the measured resistance of the coil 12 is proportional to its temperature. The measured resistance is applied to a subtractor circuit 30 which subtracts the measured resistance of the coil 12 from a set point resistance derived from a set point temperature circuit 32. The set point resistance derived from the set point temperature circuit 32 represents a desired temperature to which the coil 12 is to be heated. The output of the subtractor circuit 30 represents the difference between the set point resistance and the measured coil resistance and thus the difference between the set point temperature and the measured coil temperature.

The output of the subtractor circuit 30 is fed back to the controlled signal source 16 to control the amount of current delivered to the coil 12. Thus, if the temperature of the coil 12 is less than the set point temperature, more current will be delivered to increase the temperature of the coil 12. If the temperature of the coil 12 is greater than the set point temperature, the amount of current is quickly reduced to zero to lower the temperature of the coil 12. A special feedback circuit 50 is provided for rapid, exponential response when the actual and set point temperatures are different, yet gives proportional control when the actual temperature is close to the set point temperature as will be described in detail with reference to FIGS. 6–8.

The measured coil resistance and the set point resistance are converted to an actual temperature and a set point temperature respectively and displayed by an actual temperature display circuit 34 and a set point temperature display circuit 36 respectively.

In addition, depending upon the device 11 in which the coil 12 is incorporated, as will be described in detail hereinafter, the power delivered to the coil 12 may be measured to determine characteristics of fluid flowing past the coil 12. More particularly, a first squarer circuit 38 determines the power delivered to the coil 12. A second squarer circuit 40 squares the measured power value and sends its output to a pulsatile flow display circuit 42 and a mean flow velocity display circuit 44.

Figure 2A:
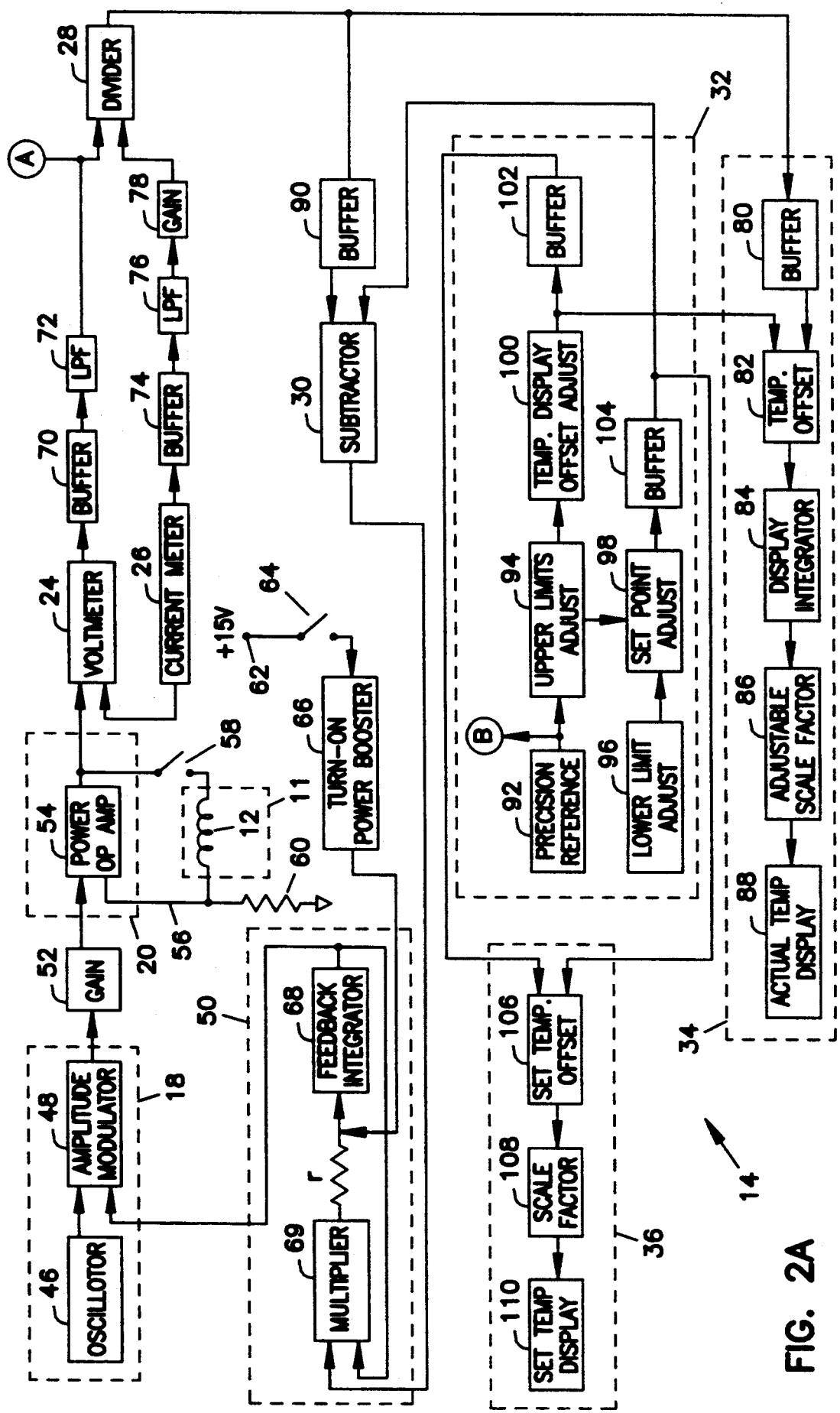
FIGS. 2a and 2b illustrate a more detailed block diagram of the apparatus shown in FIG. 1.
Figure 2B:
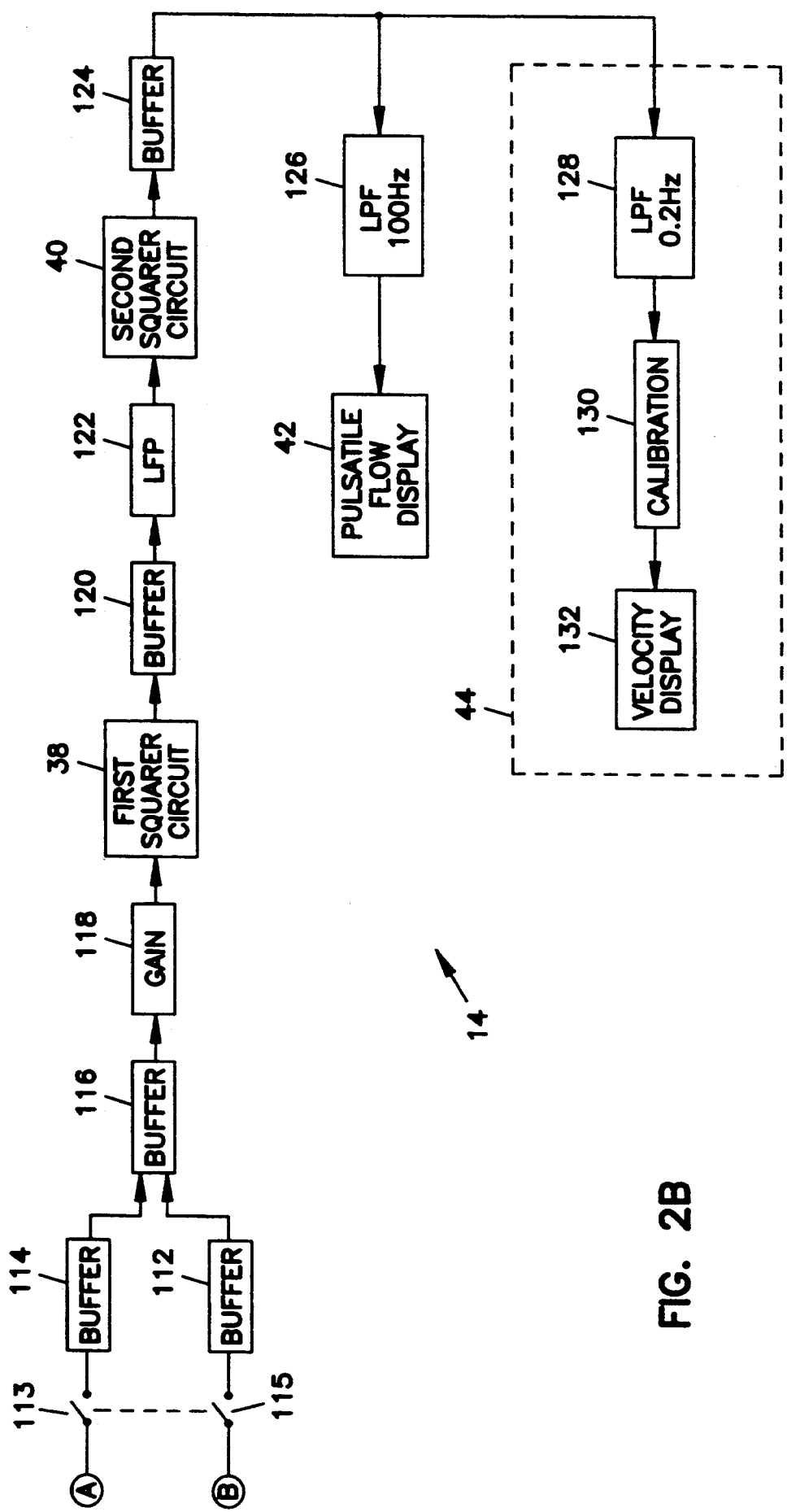

FIGS. 2a and 2b illustrate a more detailed block diagram of the apparatus 10 shown in FIG. 1. FIGS. 3a–e illustrate a specific embodiment of the apparatus 10 shown in FIGS. 2a and 2b which will be described hereinafter.

Amplitude controlled oscillator 18 includes oscillator 46 and amplitude modulator 48. Oscillator 46 preferably supplies a 25 kilohertz (kHz) signal to amplitude modulator 48, however, other frequencies may be used. The amplitude modulator 48 also receives an input signal from a feedback circuit 50 which will be described in detail hereinafter. Amplitude modulator 48 modulates the amplitude of the signal received from oscillator 46 in accordance with the feedback signal received from feedback circuit 50. The output of the amplitude modulator 48 is fed through a gain circuit 52 to the current driver 20. The current driver 20 includes a power operational amplifier ("op amp") 54.

Connected between the output of the op amp 54 and its negative input 56 through switch 58 is the coil 12 embodied in device 11. The negative input 56 of op amp 54 is connected to ground through a resistor 60. Switch 58 communicates with a heat switch 160 (FIG. 4) located on the front panel of the instrumentation housing 150 to be described in detail hereinafter. The output and the negative input 56 of the op amp 54 are applied to voltage meter 24. The negative input 56 of op amp 54 is also applied current meter 26.

A positive voltage supply 62 is supplied through a switch 64 to a turn-on power booster circuit 66. The output of the booster circuit 66 is supplied to an input of a feedback integrator 68 included in the feedback circuit 50. Switches 58 and 64 are tied together so that both switches open and close together and are controlled by the heat switch 160 (FIG. 4) located on the front panel of the instrumentation housing 150.

The voltage meter 24 measures the voltage across the coil 12 by receiving as inputs the negative input 56 and output of the op amp 54. The output of the voltage meter 24 is applied through a buffer 70 and a low pass filter 72 to one input of the precision divider circuit 28. The current meter 26 measures the current flowing through the coil 12 by receiving as an input the negative input 56 of the op amp 54. The output of the current meter 26 is applied through a buffer 74, a low pass filter 76 and gain circuit 78 to a second input of the precision divider circuit 28. The precision divider circuit 28 divides the voltage measured across the coil 12 by the current measured through the coil 12 to obtain a value proportional to the resistance of the coil 12.

The output of the divider circuit 28 is applied to the actual temperature display circuit generally referred to as 34. The actual display circuit 34 converts the measured coil resistance to a temperature value for display. The display circuit 34 includes a buffer 80 which applies the output from the divider circuit 28 to one input of a temperature offset circuit 82. The temperature offset circuit 82 also receives an input from set point temperature circuit generally referred to as 32 which is subtracted from the measured coil resistance applied by buffer 80.

The output of the offset circuit 82 is applied to a display integrator 84 which can be used to delay the display of the coil temperature by a specified amount of time. For example, if coil 12 is used to heat the inflation fluid within the balloon of a dilation catheter as will be described with reference to FIG. 11, the display integrator 84 delays the display reading preferably by four seconds. The delayed reading corresponds more closely to the temperature at the surface of the balloon which lags behind the actual coil temperature because of the thermal inertia of the inflation fluid. On the other hand, if coil 12 is used in an anemometer to measure the characteristics of a fluid flowing past the coil 12 such as its velocity as will be described with reference to FIG. 10, the delay introduced by the display integrator 84 is set to zero.

An adjustable scale factor circuit 86 converts the measured coil resistance to a temperature value preferably in terms of degree Celsius. The temperature value is then displayed by an actual temperature display 88 (FIG. 4) located on the front panel of instrumentation housing 150.

The output of the divider circuit 28 is also applied through a buffer 90 to one input of subtractor circuit 30. The subtractor circuit 30 receives another input from the set point circuit 32. The output of the subtractor circuit 30 is applied to the amplitude modulator 48 through feedback circuit 50.

The set point circuit 32 includes a precision reference circuit 92, an upper limit adjust circuit 94, a lower limit adjust circuit 96, a set point adjust circuit 98, a temperature display offset adjust circuit 100 and buffers 102 and 104. The set point adjust circuit 98 communicates with both the upper and lower limit adjust circuits 94 and 96 to select a value in a range determined by those circuits 94 and 96. The set point adjust circuit 98 communicates with a control knob 158 (FIG. 4) located on the front panel of the instrumentation housing 150. As will be described in detail hereinafter, a set point temperature is selected between a range established by the upper an lower limit adjust circuits 94 and 96 by turning control knob 158. The output of the set point adjust circuit 96 represents a selected set point temperature in terms of resistance that will be referred to as a see point resistance. The set point resistance value is applied through a buffer 104 to the subtractor circuit 30 as previously described. The set point resistance value is also applied to the set temperature display circuit 36.

The set point temperature display circuit 36 converts the set point resistance value to a temperature value for display. The set point temperature display circuit 36 includes a set point temperature offset circuit 106, a scale factor circuit 108 and a set point temperature display 110. The set temperature offset circuit 106 receives inputs from the set point adjust circuit 98 and the temperature display offset adjust circuit 100 and applies its output through scale factor circuit 108 to display 110 (FIG. 4) located on the front panel of the instrumentation housing 150.

As previously described with reference to FIG. 1, if the coil 12 is utilized in an apparatus to measure the characteristics of a flowing fluid such as its velocity, the power delivered to the coil 12 is measured. FIG. 2b illustrates the circuitry used to perform such measurements. Buffer 112 receives the output of the precision reference circuit 92 and buffer 114 receives the output of the low pass filter 72 associated with the voltage meter 24 preferably by switches 113 and 115 which are tied together to open and close together. Switches 113 and 115 can communicate with a selection switch 164 (FIG. 4) located on the front panel of the instrumentation housing 150. Selection switch 164 is provided to indicate the device 11 connected to circuitry 14 as will be described hereinafter. The output of buffers 112 and 114 are applied to an offset circuit 116 which subtracts one input from the other. Offset circuit 116 allows the mean velocity of the fluid to be calculated by providing a stable d.c. level as will be described in detail hereinafter.

The output of the offset circuit 116 is sent through a gain circuit 118 to the first squarer circuit 38. The first squarer circuit 38 performs the operation of multiplying the input with itself. The output of the first squarer circuit 38 is applied to a second squarer circuit 40 through a buffer 120 and low pass filter 122. The output of the second squarer circuit 40 is applied through a buffer 124 and low pass filter 126 to pulsatile flow display 42.

The output of the second squarer circuit 40 is also applied to the mean flow velocity display circuit 44. The mean flow velocity display circuit 44 includes a low pass filter 128, a calibration circuit 130 and a velocity display 132 (FIG. 4) located on the front panel of instrumentation housing 150, The calibration circuit 130 converts the signal received from buffer 124 which is proportional to the square of the power through coil 12 to a mean velocity value.

FIGS. 3a-e illustrate a specific embodiment of the apparatus 10 shown in FIGS. 2a and 2b. The detailed circuitry illustrated in FIGS. 3a-e is provided only as an example and not a limitation of the present invention. It is also contemplated that the circuitry represented in FIGS. 2a and 2b could be implemented using digital circuit components or a combination of digital and analog components.

Labels representing the blocks in FIGS. 2a and 2b are located over corresponding portions of the circuitry in FIGS. 3a-e. The model numbers of chips used for various elements are printed adjacent to each element. Elements whose model numbers begin with the prefix AD and OP are commercially available from the Analog Devices Corporation of Norwood, Mass. and those that begin with the prefix EL are commercially available from Elantec of Milpitas, Calif. The actual temperature display 88, set point temperature display 110 and mean flow velocity display 132 are available from Martel Corp. of Windham, N.H. as Model No. DPM 500S. The value of discrete elements such as resistors and capacitors used in the circuitry are labelled in FIGS. 3a-e and thus need not be described in detail. Of course those skilled in the art will appreciate that components available from other sources may be used.

In addition, some components may be eliminated or combined together. For example, if a direct current source is used instead of oscillator 46, the voltage meter 24 and current meter 26 shown in FIG. 3b as RSM to DC converters would be eliminated as will be described in detail with reference to FIGS. 15a-c. Also, portions of the circuitry may be eliminated if the present invention is no be used only with a particular device 11.

Only portions of the specific circuitry shown in FIGS. 3a-e will be described in detail with reference to the preferred embodiments of the present invention. The upper and lower limit adjust circuits 94 and 96, set point adjust circuit 98, adjustable scale factor 86 and calibration circuit 130 are all implemented by variable resistors or potentiometers VR1, VR3, VR2, VR5 and VR6 respectively. Certain components shown in FIGS. 3a-e will have different performance values depending upon the device 11 in which the coil 12 is embodied. For example, the value of capacitor C5 in the feedback path of feedback integrator 68 will vary to provide different time constants as will be described with reference to FIGS. 9 and 10. In addition, the bandwidth of low pass filters 72 and 76 will also vary.

Figure 4:
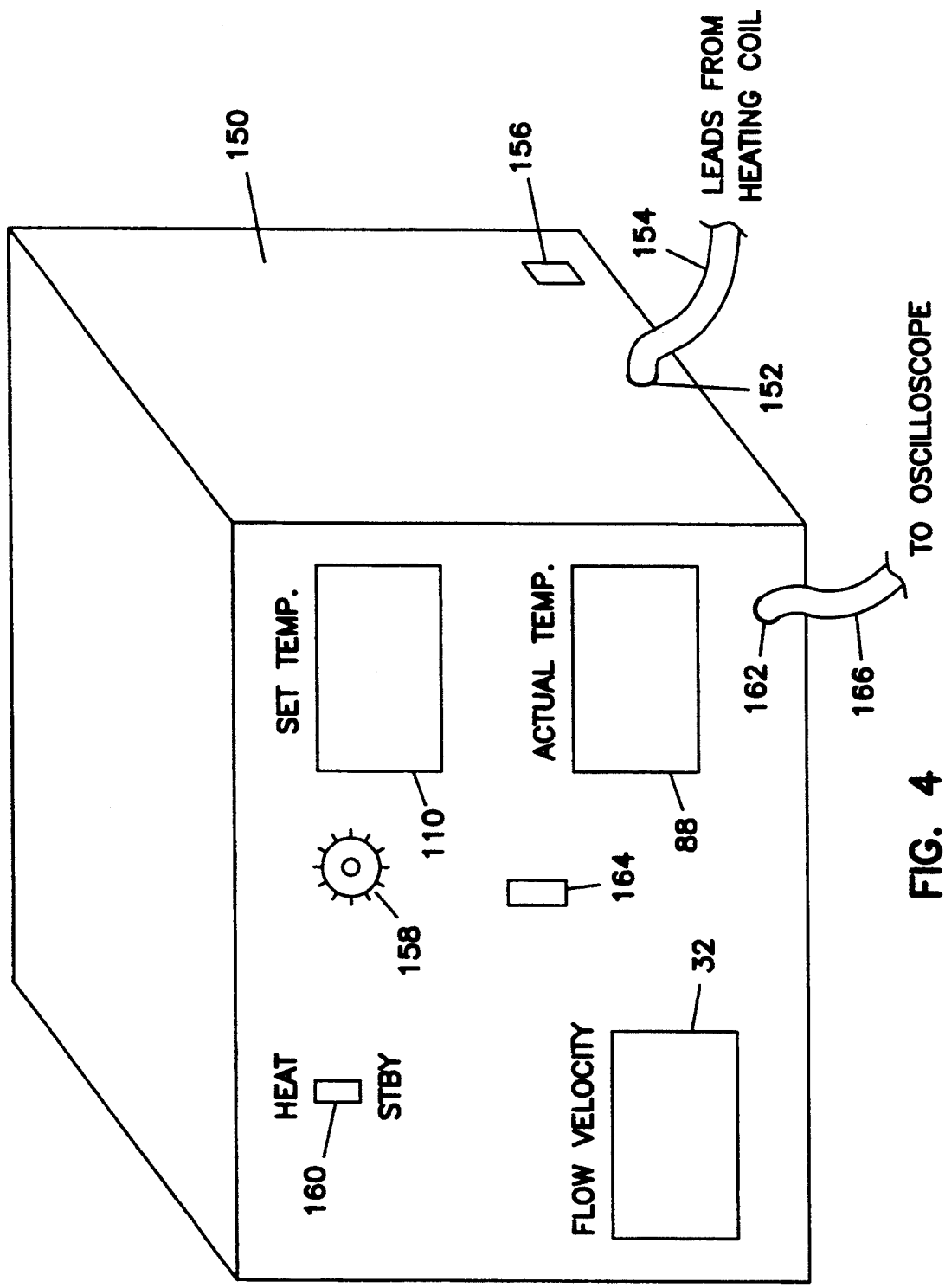
FIG. 4 illustrates the instrumentation housing which contains a portion of the apparatus shown in FIG. 1 according to a preferred embodiment of the present invention.

FIG. 4 illustrates instrumentation housing 150 which contains the circuitry 14 shown in FIG. 1 according to a preferred embodiment of the present invention. Leads (not shown) from the coil 12 are connected to the circuitry 14 through port 152 preferably by a cable 154 which will be described hereinafter. A main switch 156 provides power to the circuitry contained in housing 150. Located on the front panel of the housing 150 are several displays including the set point temperature display 110, the actual temperature display 88 and the flow velocity display 132. Also located on the front panel of housing 150 is a control knob 158, a heat switch 160 and a connection port 162. A selection switch 164 may be provided to indicate the specific device in which the coil 12 is embodied. Connection port 162 allows connection preferably by a cable 166 of a pulsatile flow display 42 such as an oscilloscope for example.

As previously described, the heat switch 160 communicates with both switches 58 and 64 shown FIG. 2a to connect coil 12 with the output of op amp 54 and the turn-on power booster circuit 66 with voltage supply 62 when the heat switch 160 is flipped to its heat setting. The control knob 158 controls the potentiometer VR2 (FIG. 3c) of the set point adjust circuit 98. The resistance of potentiometer VR2 changes as the control knob 158 is turned. The resistance established by potentiometer VR2 is used as the set point resistance to be converted to a set point temperature and displayed on the set point temperature display 110.

The operation of the circuitry 14 of FIGS. 1, 2a and 2b and 3a-e will now be described with reference to the instrumentation housing shown in FIG. 4.

A set point temperature is selected by turning control knob 158 located on the front panel of the instrumentation housing 150. The selectable range of set point temperatures is determined by upper and lower adjust circuits 94 and 96 respectively. Preferably the lower limit is set to about 40° C. and the upper limit is set to about 70° C. These limits can be altered by adjusting the variable resistors VR1 and VR3 of the upper and lower limit adjust circuits respectively. As the control knob 158 is turned, the set point temperature is displayed preferably in units of degree Celsius on the set temperature display 110. The output of the set point adjust circuit 98, however, is in terms of a set point resistance value. After a set point temperature has been selected, the heat switch 160 is flipped to its heat setting.

Flipping the heat switch 160 to its heat setting closes switches 58 and 64. Coil 12 is thus connected to the output of op amp 54 and the turn-on power booster circuit 66 is connected to the positive voltage supply 62. Connecting the turn-on power booster circuit 66 to the voltage supply 62 provides a momentary positive signal to the input of the feedback integrator 68 of the feedback circuit 50. The power booster circuit 66 ensures that upon power up the feedback signal applied to the amplitude modulator 48 will be positive. In particular, the turn-on power booster 66 provides a positive voltage on the capacitor C5 (see FIG. 3a) of the feedback integrator 68 thereby avoiding positive feedback and thus instability. Referring to the detailed circuitry of the power booster circuit 66 in FIG. 3a, when capacitor C4 is sufficiently charged, relay K1 opens thus disconnecting the output of the booster circuit 66 from the feedback integrator 68.

The power op amp 54 receives the output of modulator 48 and functions to supply the coil 12 with the appropriate amount of current to raise the temperature of the coil 12 to the set point temperature selected. The amount of current delivered to the coil 12 will thus vary depending upon the output of the modulator 48 which in turn reflects a comparison between the actual measured temperature of the coil 12 and the selected set point temperature as will be fully explained hereinafter.

Figure 5:
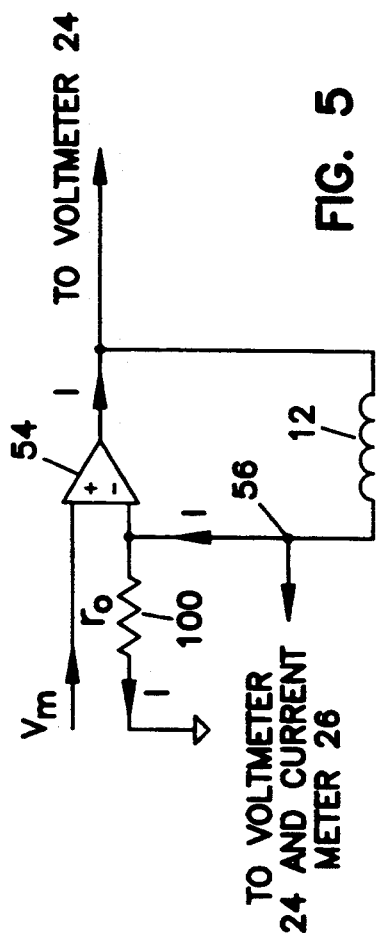

A detailed description of the operation of the power op amp 54 will now be given with reference to FIG. 5. As previously described, the coil 12 is provided in the feedback loop of the op amp 54. The negative input 56 of op, amp 54 is connected to ground through a precision power resistor 60. The op amp 54 is used in its transconductance (i.e. voltage-to-current) configuration as is well known to those skilled in the art. The input signal $V_m$ supplied by modulator 48 through gain circuit 52 is applied to the positive input of the op amp 54. The output and negative input 56 of the op amp 54 are applied voltage meter 24 which preferably is a true r.m.s. voltmeter. In addition, the negative input 56 is also sent to a current meter 26 which is also preferably a true r.m.s. current meter.. The voltage meter 24 measures the voltage across the heating coil 12 which equals the voltage applied by the modulator 48 ($V_m$) multiplied by the resistance of the coil 12 ($r_{coil}$), divided by the resistor 60 ($r_0$) which is represented by equation (1) below:

$$\left( \frac{V_m r_{coil}}{r_0} \right) \quad (1)$$

The current meter 26 measures the current running through the coil 12 which is represented by equation (2) below:

$$\left( \frac{V_m}{r_0} \right) \quad (2)$$

The precision divider circuit 28 divides the measured voltage represented by equation (1) by the measured current represented by equation (2) to generate an output equal to the resistance of the coil 12 ($r_{coil}$). Before the measured voltage and current are applied to the precision divider circuit 28 they are passed through buffers and low pass filters, in addition, the measured current is also passed through a gain circuit, to provide clean signals to the precision divider circuit 28 which are within its operating voltage range.

As previously described the resistance of the coil 12 varies linearly with its temperature, therefore, the output of the precision divider circuit 28, which is a measure of the resistance of the coil 12, is directly proportional to the temperature of the coil 12. The output of the divider circuit 28 is applied to the subtractor circuit 30 where it is subtracted from a set point resistance value representing the selected set point temperature applied by the set point temperature circuit 32. The output of the subtractor circuit 30 which represents the difference between the set point temperature and the measured coil temperature is then applied to the feedback circuit 50 which will now be described in detail.

Figure 6:
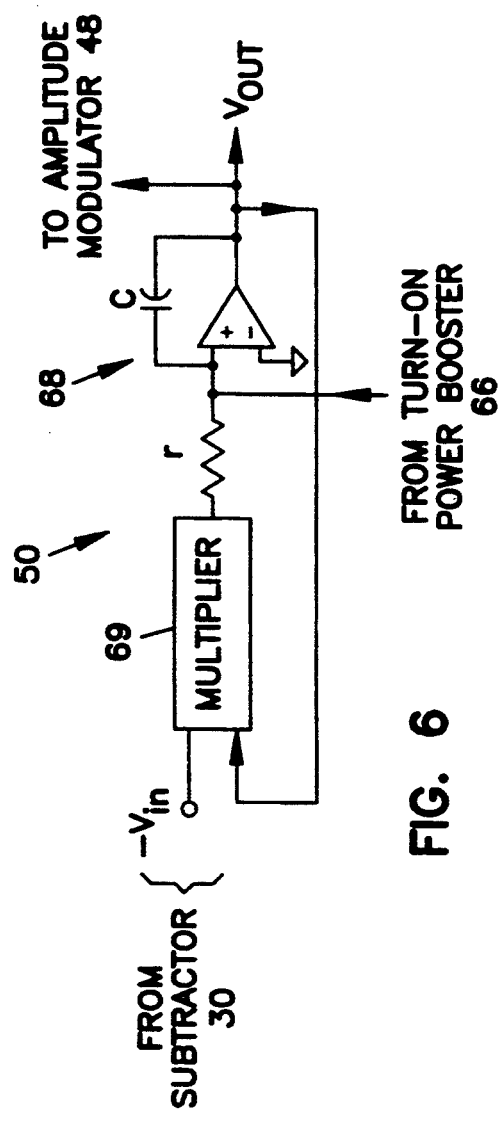
FIG. 6 is a detailed schematic of a feedback circuit used in the apparatus of the present invention.

FIG. 6 illustrates in detail the feedback circuit 50 shown in FIG. 2a. Feedback circuit 50 includes feedback integrator 68 and multiplier 69. The feedback integrator 68 includes an operational amplifier with a capacitor (C) and resistor (r) as is well known to those skilled in the art. The output of the subtractor circuit 30 ($-V_{in}$) is supplied to the multiplier 69. As previously described $-V_{in}$ is proportional to the difference between the temperature of the coil ($T_{coil}$) and the selected set point temperature ($T_{set}$). The other input of the multiplier 69 receives as an input the output of the feedback integrator 68 ($V_{out}$). The multiplier 69 multiplies $-V_{in}$ by $V_{out}$ and applies it to the feedback integrator 68. The output $V_{out}$ from the feedback circuit 68 is represented by the equation (3) below:

$$V_{out} = \frac{1}{rC} \int \frac{V_{in} V_{out}}{10} dt, \quad (3)$$

where the output of the multiplier is $V_{in}V_{out}/10$ volts. An approximate solution to equation (3) is represented by equation (4) below:

$$V_{out} = k \cdot \exp\left( \frac{V_{in} \cdot t}{10rC} \right) \quad (4)$$

where (k) represents a constant and (t) represents time. Therefore, depending upon the value of $V_{in}$, which is proportional to the difference between $T_{coil}$ and $T_{set}$, $V_{out}$ will vary as shown in the graphs of FIGS. 7 and 8.

Figure 7:
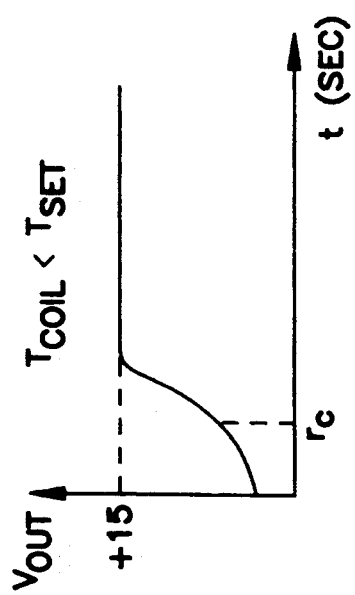
FIG. 7 is a graph illustrating the output of the feedback circuit shown in FIG. 6 for a first condition.

FIG. 7 illustrates the value of $V_{out}$ as a function of time when the temperature of the coil 12 is less than the selected set point temperature. The value of $V_{out}$ will increase exponentially at a rate determined by the resistor and capacitor (rC) of the feedback integrator 68 to the maximum voltage, i.e. the voltage of supply 108 (FIG. 2a) which is preferably 15 volts. As previously described, the proper time constant (rC) will vary depending upon the device 11 in which the coil 12 is embodied. As $V_{out}$ increases, the amplitude modulator 48 supplies the op amp 54 with a greater voltage which increases the current applied to the coil 12 thereby increasing its temperature.

Figure 8:
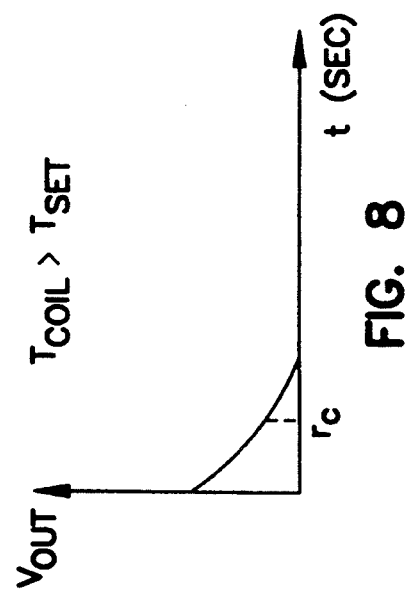
FIG. 8 is a graph illustrating the output of the feedback circuit shown in FIG. 6 for a second condition.

FIG. 8 illustrates the value of $V_{out}$ as a function of time when the temperature of the coil 12 is greater than the selected set point temperature. The amplitude modulator 48 exponentially reduces the voltage applied to the op amp 54 to zero so that no current flows through the coil 12 thereby reducing its temperature. Thus, when the actual temperature and set point temperature are different, a rapid, exponential response is provided and yet when the actual temperature is close to the set point temperature, proportional control is achieved. Therefore, unlike a typical thermostat which fluctuates between on and off when the measured temperature is close to a selected set point temperature, the feedback circuit 50 provides smooth temperature control because $V_{out}$ is proportional in the first order to the difference between the temperature of the coil 12 and the selected set point temperature. Thus when the temperature of the coil 12 approaches the set point temperature, the control provided by feed back circuit 50 is almost linear as seen in FIGS. 7 and 8.

As previously described in order to display the temperature of the coil 12 and the set point temperature, the coil and set point resistances output from the subtractor circuit 30 and the set point adjust circuit 98 respectively must be properly scaled and calibrated. Referring to FIG. 2a the measured resistance of the coil 12 is converted to a temperature by subtracting a constant derived from the temperature display offset adjust circuit 100 from the measured resistance in the temperature offset circuit 82. The output of the temperature offset circuit 82 is then sent to a display integrator 84 which may delay the temperature display reading relative to the actual coil temperature depending upon the device 11 in which the coil 12 is embodied. The output of the integrator 84 is multiplied by the adjustable scale factor circuit 86 which converts the resistance to a temperature value 84 for display by the actual temperature display 88. Alternatively, the actual temperature of the coil 12 can be displayed by eliminating the display integrator 84.

To display the set point temperature, the output of the set point adjust circuit 98 is applied to the set point temperature offset circuit 106 where the same offset value derived from the temperature display offset adjust circuit 100 is subtracted. The scale factor circuit 108 multiplies the output of the offset circuit 106 by a scale factor to convert it to a temperature value where it is then displayed on the set temperature display 110. In principle, the scale factor set by scale factor circuit 108 and adjustable scale factor circuit 86 are identical for the set point and actual coil temperature displays, however, slight differences in fixed resistor values in both circuits can lead to readings which are different by a few degrees at equilibrium. The adjustable scale factor circuit 86 trims out this difference.

Figure 3A:
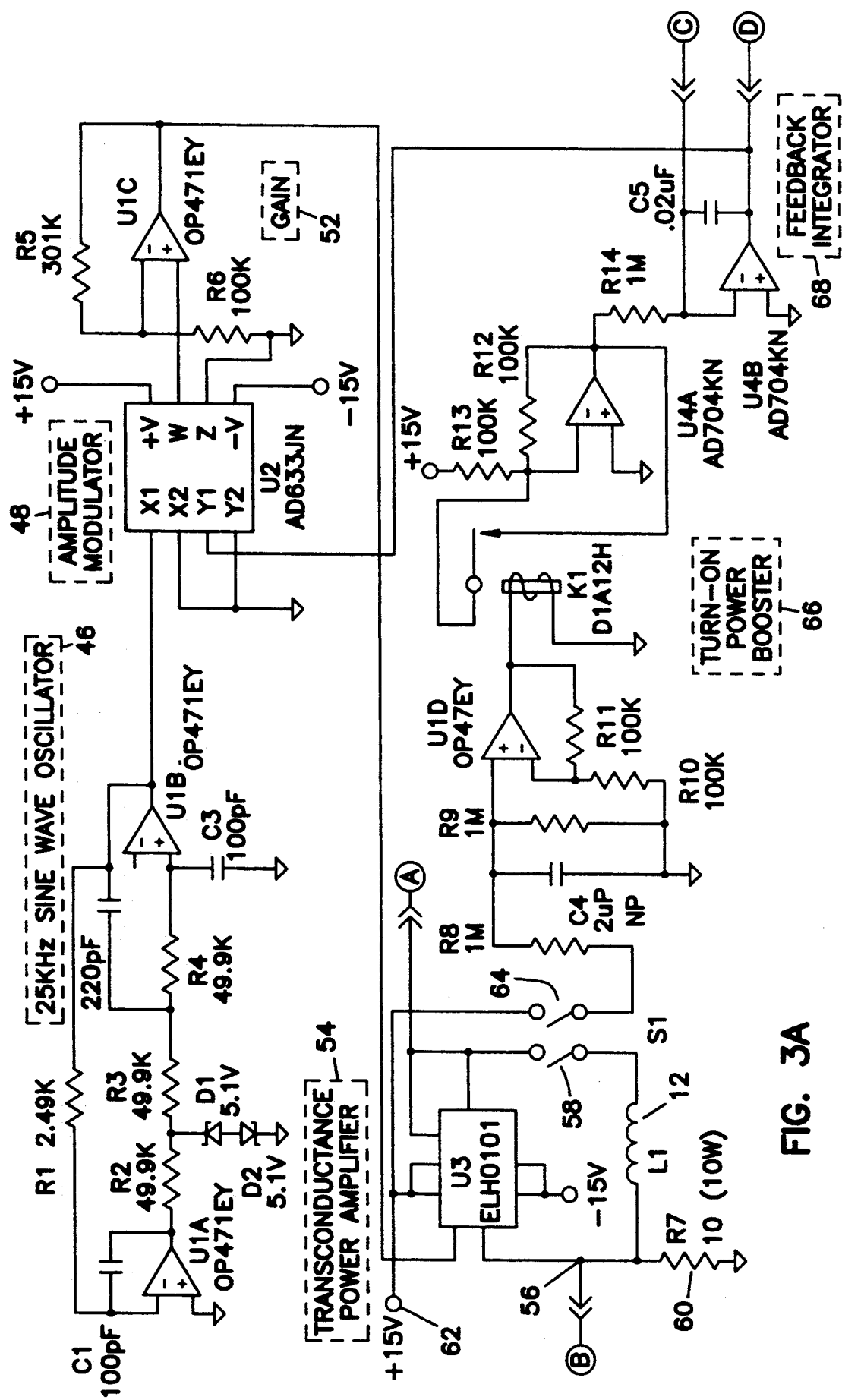
FIGS. 3a through 3e illustrate a specific embodiment of the apparatus shown in FIGS. 2a and 2b.
Figure 3B:
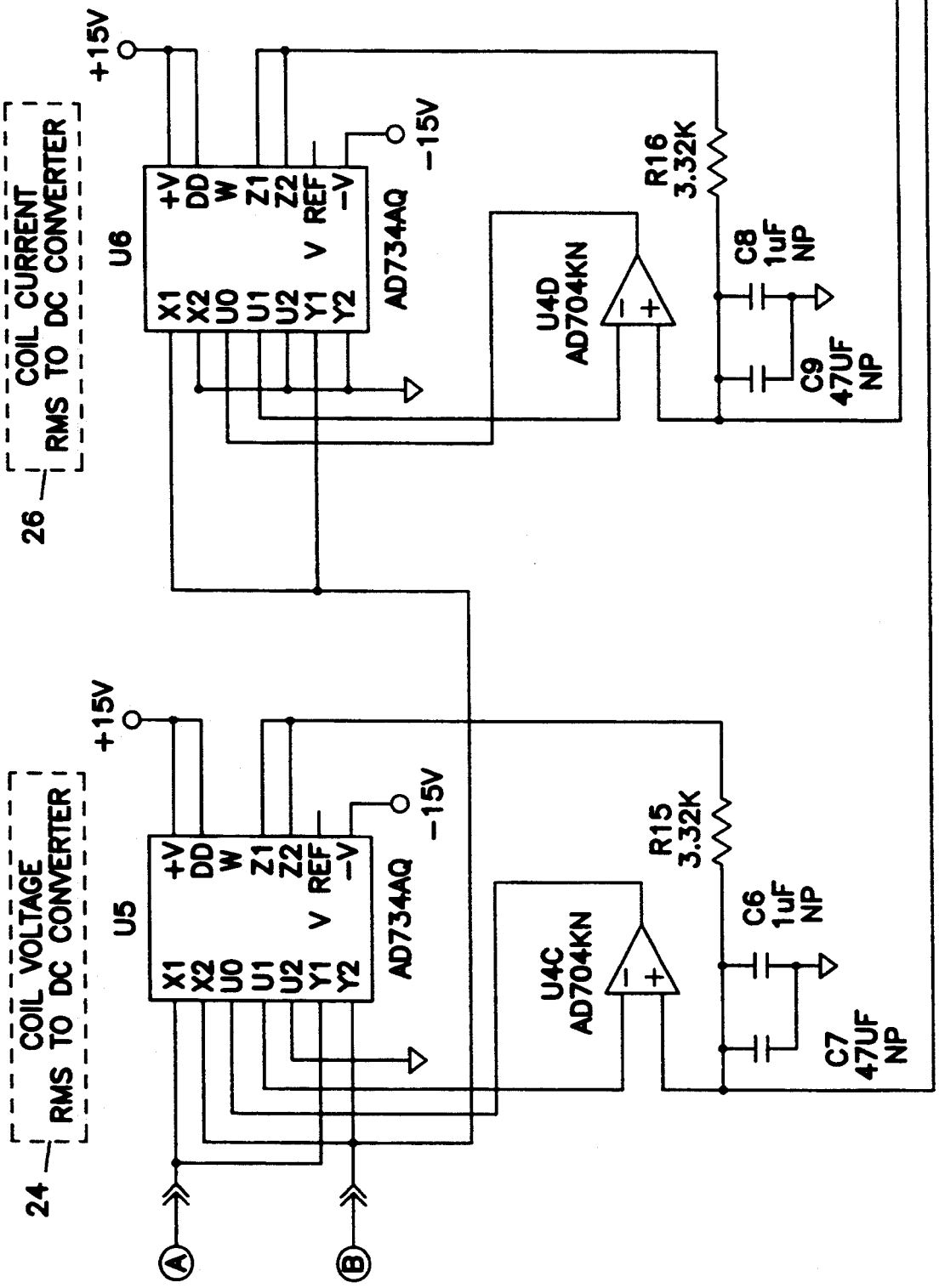
Figure 3C:
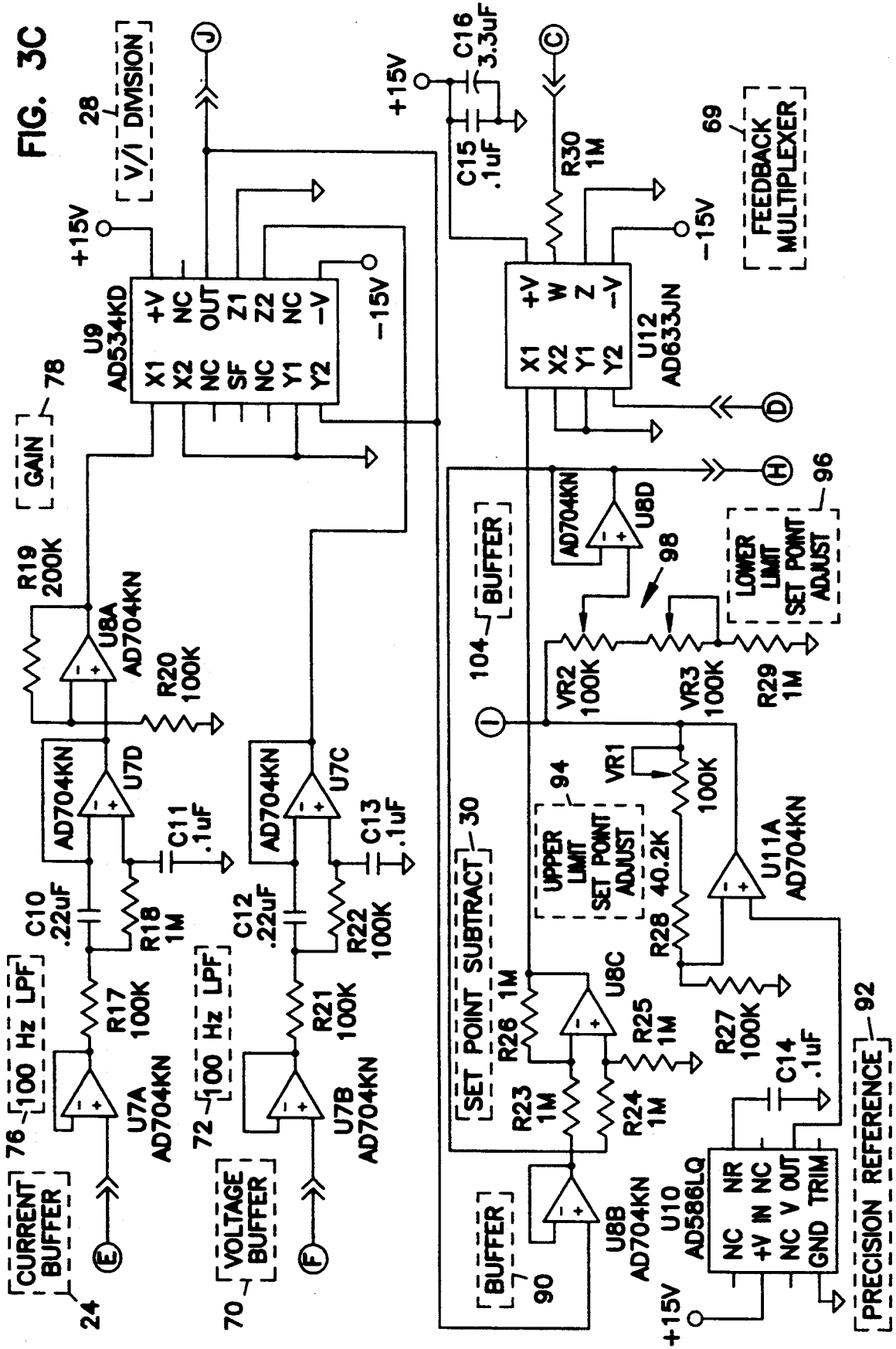
Figure 3D:
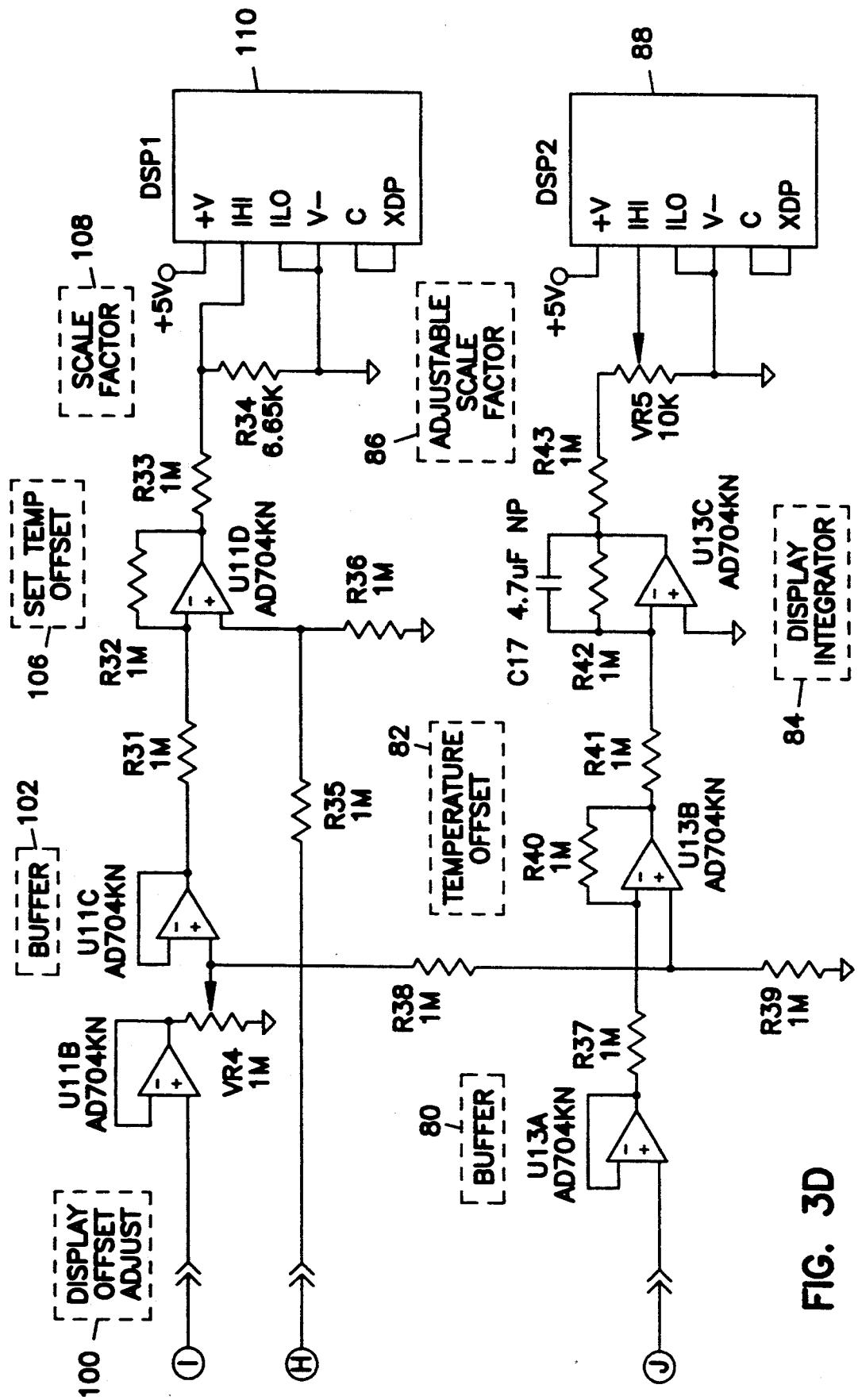
Figure 3E:
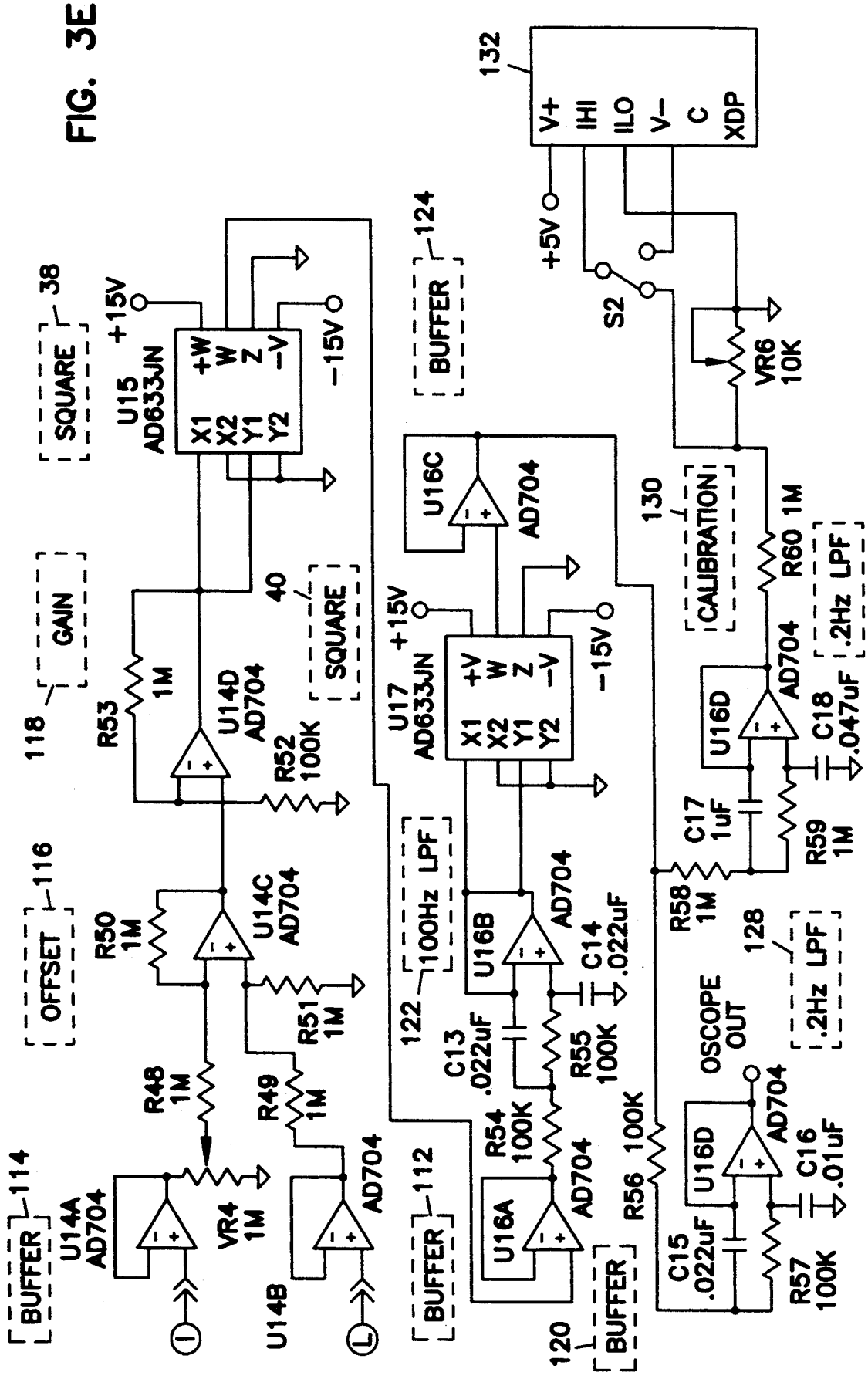

The calibration of the circuitry of the present invention will now be described. A thermocouple is attached to either the coil 12 itself or to the balloon surface, if the coil 12 is placed in a dilation catheter. A heat sink compound is applied at the thermocouple attachment site to ensure that the thermocouple correctly reads the temperature at the attachment site. The leads (not shown) of the coil 12 are connected to port 152 of the housing 150 by cable 154. The control knob 158 is turned fully counter-clockwise to its lowest value. The main switch 156 is turned on and then the heat switch 160 is flipped to its heat setting. The thermocouple temperature is observed as the temperature of the coil 12 is raised. If the thermocouple temperature rises above a maximum desired value, the upper limit established by the upper limit adjust circuit 94 is lowered by adjusting potentiometer VR1 (FIG. 3c). Next the control knob 158 is gradually turned clockwise, and the upper limit adjust circuit 94 is lowered if the thermocouple temperature exceeds its maximum desired value. After the control knob 158 reaches its full clockwise position, if the temperature of the thermocouple is below the desired maximum value, the upper limit is raised until the desired maximum temperature is achieved. Now with the control knob 158 turned fully clockwise, the thermocouple temperature is equal to the desired maximum balloon temperature.

Next the control knob 158 is turned fully counter-clockwise. The potentiometer VR3 (FIG. 3c) of the lower limit adjust circuit 96 is adjusted until the thermocouple temperature is the lowest desired balloon temperature. The range of achievable temperatures has now been set. Next the control knob 158 is turned midway between the lowest and highest temperatures set by the lower and upper limit adjust circuits. The variable resistor VR4 (FIG. 3d) of the temperature display offset adjust circuit 100 is adjusted until the set point temperature display 110 reading is equal to the thermocouple reading. Finally the variable resistor VR5 (FIG. 3d) of the adjustable scale factor circuit 86 is adjusted until the actual temperature display 88 reading is the same as the set point temperature display 110 reading. The circuitry is thus calibrated and ready for use once the thermocouple is removed.

Figure 9:
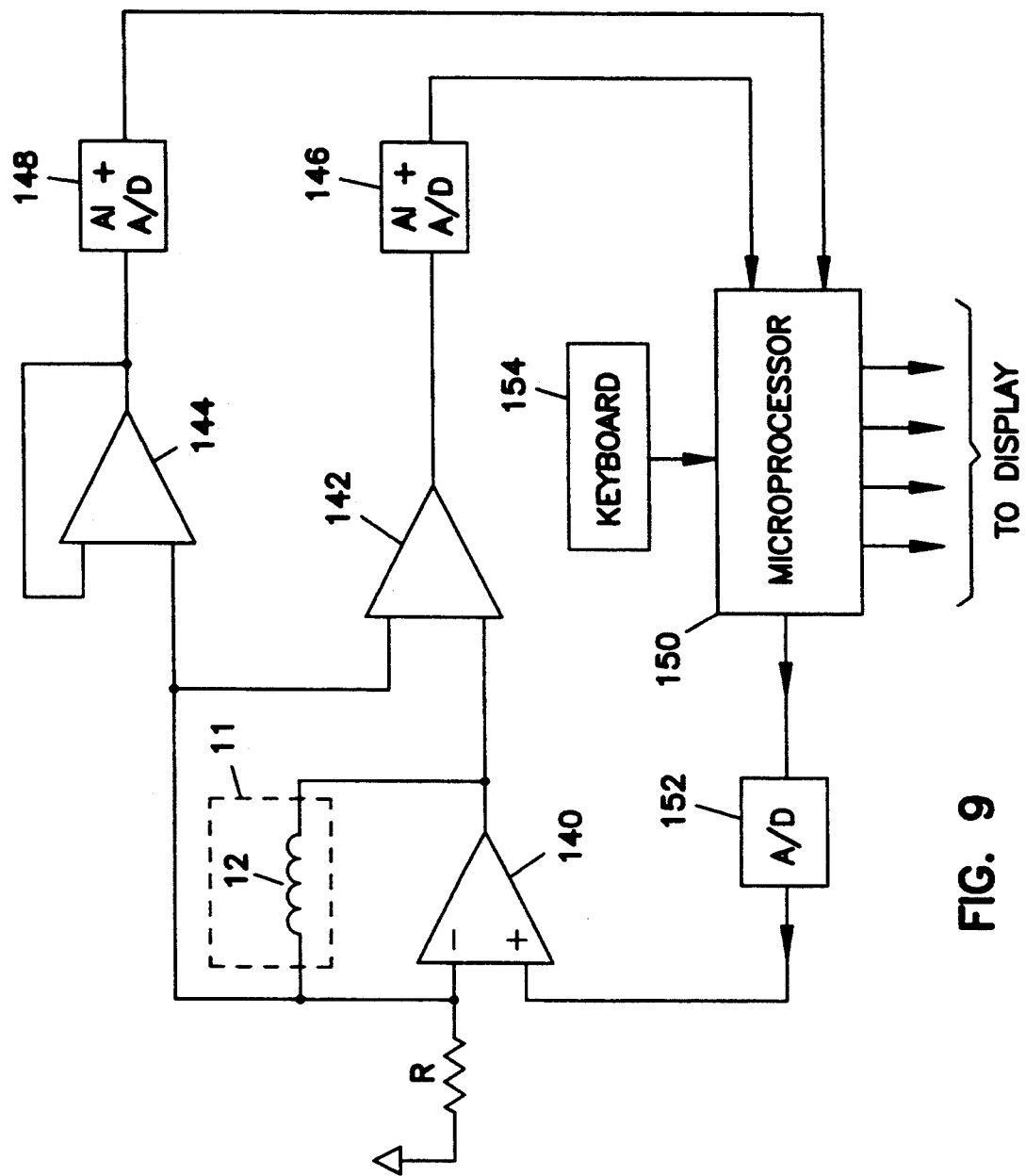
FIG. 9 illustrates a block diagram of an apparatus for performing intravascular therapy and diagnostics according to another preferred embodiment of the present invention.

A substantial portion of the circuitry 14 shown in FIGS. 3a–e may be replaced by a microprocessor. FIG. 9 illustrates a block diagram of an apparatus for performing intravascular therapy and diagnostics according to another preferred embodiment of the present invention. The heating element in the form of coil 12 is connected to a power op amp 140 in the same manner described above. The output and the negative input of op amp 140 are sent to a differential amplifier 142. The negative input of op amp 140 is sent to a buffer amplifier 144. Amplifier 144 measures the current flowing through coil 12 and amplifier 142 measures the voltage across the coil 12. The outputs of amplifiers 142 and 144 are sent to antialiasing filter and analog-to-digital converter circuits 146 and 148 respectively where the measured current and voltage are converted to digital values. The output of both circuits 146 and 148 are inputted to a microprocessor 150. An output of the microprocessor 150 is converted to an analog value by digital-to-analog converter circuit 152 and applied to the positive input of power op amp 140 to control the current flowing through coil 12. Other outputs of microprocessor 150 are sent to displays such as those previously described.

The microprocessor 150 performs the same functions as are performed by circuitry 14 described above such as determining the measured resistance and comparing it to a set point resistance, supplying the appropriate feed back signal to control op amp 140 and converting signals so that they may be appropriately displayed. In addition, a keyboard 154 may be provided so that a user can enter data such as the set point temperature and the particular device 11 currently in use through a menu driven program run by software in the microprocessor 150.

Specific examples of a device 11 in which coil 12 is incorporated according to preferred embodiments of the present invention will now be described. The circuitry 14 described above is used to control the temperature of the coil 12 and display information collected by circuitry 14 in accordance with the device 11 in which the coil 12 is incorporated as will become clear from the following description.

Figure 10:
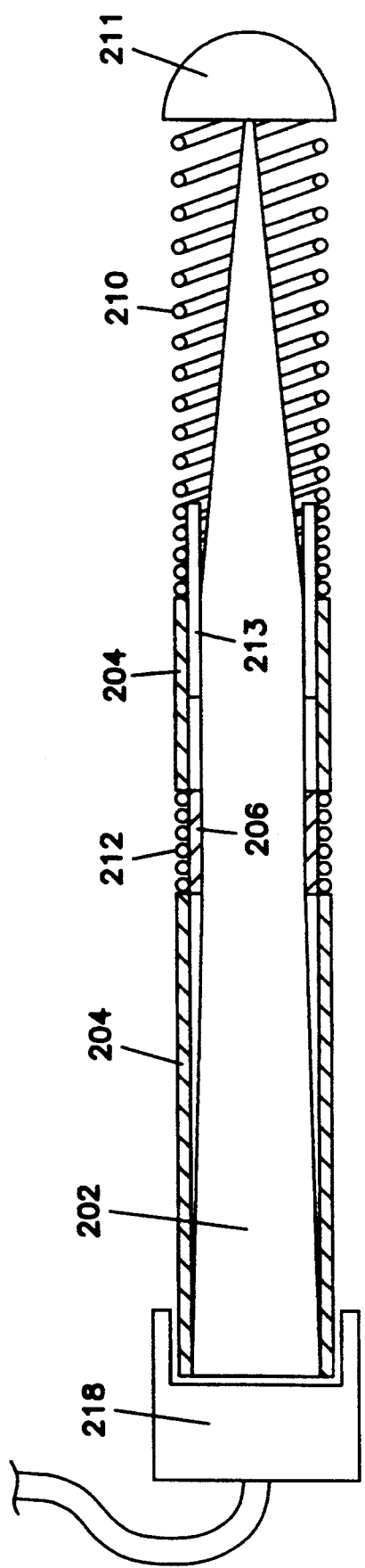
FIG. 10 illustrates a schematic of a modified guidewire usable with the apparatus of FIG. 1 according to a first preferred embodiment of the present invention.

FIG. 10 illustrates a schematic of a modified guidewire 200 usable with the apparatus of FIG. 1 according to a first preferred embodiment of the present invention. In a preferred embodiment the guidewire 200 includes a core wire 202 made of stainless steel having a length of about 180 cm. The core wire 202 includes a proximal portion of relatively uniform diameter preferably of about 0.018 inches and a distal portion of reduced and tapered diameters. The reduced and tapered diameter of the core wire 202 provides greater flexibility toward the distal end of the guidewire 200. The construction of the guidewire 200 may differ with regard to the degree of flexibility desired in the distal portion. The degree of flexibility is determined by the number, length, and degree of tapers in the core wire 202. In a most distal portion of the core wire 202, the core wire 202 is flattened.

The distal portion of the guidewire 200 also includes a coil spring 210 that surrounds the core wire 202 along the distal end thereof. The coil spring 210 is composed of a radiopaque material. Specifically, the coil spring 210 is composed of a platinum alloy having 92% platinum and 8% tungsten. The distal end of the coil spring 210 is connected to the distal end of the core wire 202 by means of a weld that forms a rounded distal tip 211. The coil spring 210 is approximately 0.93 to 1.38 inches in length.

A jacket 204 surrounds part of the distal portion of the core wire 202. The jacket 204 is preferably formed of a blend of nylon and polyether, commercially available under the tradename PEBAX from Atochem of Birdsboro, Pa. The jacket 204 is approximately 10.5 to 11 inches in length and has an inner diameter of about 0.015 inches and an outer diameter of about 0.018 inches. A support tube 206 is located in an interrupted section of the jacket 204, proximal to coil spring 210. The support tube 206 is formed of polyimide or any other heat resistant material such as TEFLON and has an inner diameter of about 0.006 inches, an outer diameter of about 0.015 inches. The support tube 206 is bonded to core wire 202 and to jacket 204 on its proximal and distal ends using an adhesive such as URETHANE 3507 available from the H. B. Fuller Company of St. Paul, Minn. or MASTER BOND 295 available from MasterBond, Inc. of Hackensach, N.J. Heating element 212 is wound on support tube 206 as described hereinafter. The outside diameters of the jacket 204, the heating element 212 and the spring coil 210 are substantially equal forming a smooth transition between these elements.

A bridge member 213 is located around the core wire 202 at the location where the distal end of the jacket 204 meets the spring coil 210. The bridge 213 is a small cylindrical hypotube of 304 stainless steel that fits over the core wire 202. The outer diameter of the bridge member 213 corresponds to the inner diameter of the jacket 204 and the length of the bridge member 213 is about 0.030 inches. The bridge member 213 facilitates alignment between the jacket 204 and the spring coil 210.

A coating is applied to the distal portion of the guidewire 200, approximately the distal 16 to 18 inches, to provide a uniform, low-friction surface along the distal portion of the guidewire 200. The distal portion corresponds to the location of the jacket 204, support tube 206 and coil spring 210 of the guidewire 200. Preferably the coating is composed of silicone oil and a modified moisture curable polydimethylsiloxane.

The proximal portion of the core wire 202 is coated with a low friction material such as TEFLON. The low friction coating extends along almost the entire length of the proximal portion of the core wire 202 from within approximately 1.0 inch of the proximal end of the jacket 204.

A heating element in the form of a coil 212 is wound on the exterior surface of the support tube 206. In a preferred embodiment, the heating element in the form of coil 212 is formed from a 0.001 inch diameter silver wire bifilarly wound around the exterior of support tube 206. The two strands of the bifilar pair are individually insulated with about 0.0001 inch of polyurethane. Silver has two properties that cause it to be a preferred material for use with the circuitry 14 of the present invention. First, the resistance of a silver wire varies linearly with its temperature over an operating range of about 0° C. to about 100° C. Second, the resistance of a silver wire changes about 0.38% per degree Celsius which is a relatively large temperature coefficient. Other materials which have the two properties described above may also be used. The wire is wound bifilarly around support tube 206 in order to reduce the inductance of the coil 212 upon receipt of the alternating current signal from current driver 20. Preferably, the wire is wound about 320 turns around the support tube 206 so that the coiled region has a length of about 0.40 inches and an outer diameter of about 0.018 inches. The bifilar silver wire is specified to have a highly uniform resistance per unit length and a repeatable temperature coefficient so that a 1 degree Celsius accuracy in the temperature calibration is achieved by cutting the length of bifilar silver wire to an accuracy of 0.1 inches. This has proven to be successful and a 1 degree Celsius accuracy has been maintained over many heating coils without making component changes or adjustments in the electronics. The bifilar silver wire is available from H. P. Reid Co. of Palm Coast, Fla. Leads 214 extend from the coil 212 and travel to the proximal end of the guidewire 200 as will be described in detail hereinafter where they are connectable to the circuitry 14 located in housing 150.

Several examples of ways to extend the leads 214 from the coil 212 to the proximal end of the guidewire 200 will be described. These examples are for illustration purposes only and are not intended as a limitation. One approach is to use a hollow guidewire core 202 and extend the leads 214 from the coil 212 through the space formed between the exterior of the core wire 202 and the jacket 204 and through an opening 216 to the interior of the guidewire core 202 as shown in FIG. 10. A hollow guidewire core can be formed from a superelastic material formed from a nickel/titanium alloy commercially available as NITINOL from the Raychem Corporation of Menlo Park, Calif. Forming the guidewire core of such a superelastic material allows the center of the guidewire to be hollow while retaining the mechanical characteristics required of a guidewire. An alternative to forming the entire guidewire core 202 from nitinol is to create a composite guidewire core formed by braiding fine stainless steel or NITINOL wires in a matrix of polyimide or TEFLON to form a hollow tube. The braid of superelastic material gives the hollow guidewire the required mechanical characteristics.

In addition, another approach is to layer conductors on the exterior surface of a standard guidewire to form the leads 214 of the coil 212. Because the layering will increase the overall diameter of the guidewire, an undersized guidewire is chosen preferably having an 0.014 inch diameter at its proximal end. A layer of conductive material, preferably gold, is plated to the exterior of the guidewire preferably followed by a layer of insulative material, such as polyimide followed by another layer of conductive material and another layer of insulative material Such a technique for forming leads along a guidewire was described in U.S. Ser. No. 07/969,743 filed Oct. 30, 1992 entitled "Vibration Sensing Guidewire" which is assigned to the assignee of the present invention, the entire disclosure of which is incorporated herein by reference.

Still another approach is to braid insulated electrical wires over an undersized guidewire for example a 0.014 inch diameter wire, and TEFLON coat the braided wire to form a larger diameter wire, for example, a 0.018 inch diameter wire.

Still another approach is to allow the leads 214 of the coil 212 to form part of the guidewire along with NITINOL wires of varying length to achieve an appropriately tapered core. Fine steel or NITINOL wires are then braided over the core in a TEFLON or KYNAR or polyimide matrix to form a guidewire with appropriate mechanical performance.

The coil 212 of the guidewire 200 communicates with circuitry 14 contained in instrumentation housing 150 preferably by a cable 154 connected between port 152 and an electrical connector 218 to which leads 214 are connected on the proximal end of guidewire 200. An example of a connector can be found in U.S. Ser. No. 07/969,743 previously referred to.

In general, the circuitry 14 of the preferred embodiment of the present invention measures the power required to keep the coil 212 at a fixed temperature above the ambient temperature of the fluid in which it is placed. It has been found that the velocity of the fluid is proportional to the square of the power required to keep the coil 212 at that fixed temperature. Preferably the coil temperature is maintained 5° C. above the ambient temperature of the fluid, which for blood is about 37° C. To observe the pulsatile flow of the fluid, a rapid response from the circuitry is required. To achieve such a rapid response, the time constant of the feedback integrator 68 is chosen to be 0.01 seconds by using a capacitor C5 (FIG. 3a) having a value of about 0.001 μF. In addition, the cut-off frequency of the low pass filters 72 and 76 is chosen to be about 100 Hz. The bandwidth of the filters is altered by changing the value of resistors R17 and R18 and R21 and R22 and/or capacitors C10 and C11 and C12 and C13 (FIG. 3c) as is known by those skilled in the art.

The operation of the circuitry 14 will now be described with reference to the guidewire 200 of FIG. 10. A set temperature preferably 5° C. above the ambient temperature of the fluid is selected by adjusting the control knob 158 on the front panel of the instrumentation housing 150. If various devices employing a heating element according to the present invention are to be connected to instrumentation housing 150, the selection switch 164 is provided to indicate which device is currently being used. With reference to the guidewire catheter of FIG. 10, the selection switch 164 can communicate with switches 113 and 115 (FIG. 2b) to connect the power measuring part of the circuitry to the main portion of the circuitry shown in FIG. 2a. In addition, the correct value of capacitor C5 in the feedback integrator 68 and elements of the low pass filters 72 and 76 are chosen for this particular application. Those skilled in the art will appreciate that various values of capacitors and other fixed elements can be provided in a manner to be selectable by switch 164 in accordance with the particular device being used. In the digital embodiment of FIG. 9, switch 164 (or an appropriate entry on a keyboard 154) selects software appropriate to the particular device being used.

The guidewire 200 is properly positioned in an artery by any conventional technique known to those skilled in the art. Once the guidewire 200 is properly positioned, the heat switch 160 is flipped to its heat setting thereby supplying coil 212 with current from op amp 54 to raise its temperature to the selected set point temperature. Unlike the bridge circuits associated with the prior art anemometers which required the power supply to deliver equal current to both arms of the bridge, the power supply of the present invention only needs to supply current to coil 212 and resistor R7 thus reducing the power needed to operate the circuitry of the present invention. This allows smaller components to be used thereby reducing the overall size of the system.

In order to obtain a mean velocity value, a stable d.c. level must be maintained or, in other words, a zero reading should be obtained when there is no velocity, i.e. equilibrium conditions. However, because the coil 212 is to be maintained 5° C. above the ambient temperature of the fluid, there will always be a voltage across the coil 212 even under equilibrium conditions. In order that this voltage does not register as a velocity, the output of the precision reference circuit 92 is subtracted from the voltage measured across the coil 212 in offset circuit 116 (FIG. 2b). The offset circuit 216 is adjusted so that it has a zero output when there is no flow. Thus the output of the offset circuit 116 only reflects the change in voltage across the coil 212 resulting from fluid flowing past the coil 212. This ensures that the incremental power required to maintain the temperature of the coil 212 at the set point temperature while the fluid flows past the coil 212 is being measured.

Therefore, unlike the ultrasound guidewires previously described, the guidewire 200 of FIG. 9 forms a guidewire anemometer which can accurately measure the mean velocity because the system has a stable, repeatable d.c. zero level. In addition, unlike the above-described ultrasound guidewires which measure the component of the velocity along the sensor axis, coil 212 of the present embodiment eliminates this angle dependence.

The output of the second squarer circuit 40 can be displayed two ways. An output is taken preferably through a 100 Hz low pass filter 126 to observe the instantaneous blood flow changes associated with pulsatile flow. Preferably this output can be displayed on the screen of an oscilloscope (not shown). The oscilloscope may be connected to the circuitry of the present embodiment through oscilloscope port 162 located on the front panel of the instrumentation housing 150 preferably by cable 166. The mean flow velocity can also be displayed on a flow velocity display 132 located on the front panel of housing 150 by low pass filtering and calibrating the output of the second squarer circuit 40. The low pass filter 128 preferably has a long time constant, e.g. 5 seconds, or a bandwidth of 0.2 Hz.

An advantage of the use of the circuitry of the preferred embodiment over the bridge circuits used in prior art anemometers is the ability to measure actual temperature. By using a heating element whose temperature is proportional to its resistance, an actual temperature measurement can be made. The bridge circuits of the prior art measure the bridge imbalance voltage rather than the resistance of the heating element and thus do not actually measure temperature.

It will be clear to those skilled in the art, that alternate flow sensing methods employing thermal transport phenomena could be integrated onto the guidewire in place of the anemometer coil 212. The anemometer method disclosed above has the advantage of measuring blood flow velocity using only two electrical connections to a single coil which integrates smoothly into the guidewire distal geometry. An alternate technique would use two coils separated by a known and fixed distance. Pulses of heat would be applied to the proximal coil. The distal coil of silver wire would be electrically configured as a resistance thermometer, and would receive the heat pulses a short time after being sent by the proximal coil. Blood velocity could then be determined by dividing the distance between the coils by the time elapsed between the proximal coil sending a heat pulse and the distal coil receiving the heat pulse. The two coils could share a common ground, so that two coils and three lead wires would be required for implementation.

Alternatively heat could be applied continuously to the proximal coil at a level necessary to keep the temperature of the distal coil a given small increment, for example 0.5 degree Celsius, above ambient blood temperature. The power required to keep the distal blood temperature elevated will be proportional to the volumetric blood flow rate. An advantage of this method is that the physician may prefer to measure volumetric flow (e.g. ml/min). A third proximal thermometer might be required to measure ambient blood temperature which will vary from person to person and over time. This method has been applied to the measurement of continuous cardiac output as described in PCT Application No. WO 92/22240, published Dec. 23, 1992, entitled "Heated Catheter for Monitoring Cardiac Output" by Timothy J. Hughes which is incorporated herein by reference.

Figure 11:
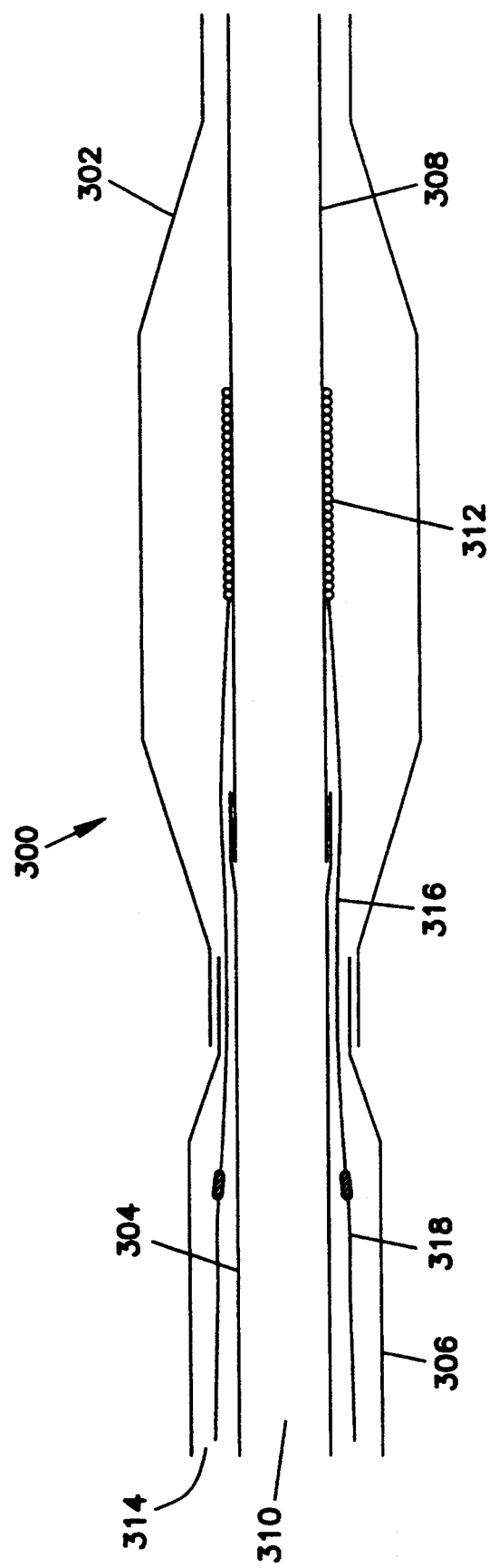
FIG. 11 illustrates a schematic of a modified dilation catheter usable with the apparatus of FIG. 1 according to a second preferred embodiment of the present invention.

FIG. 11 illustrates a schematic of a dilation catheter modified to incorporate a heating element according to a second preferred embodiment of the present invention. The catheter 300 includes a balloon 302, inner tubular member 304, outer tubular member 306 and transition tubular member 308. The transition member 308 is connected to the distal end of the inner tubular member 304 to form a guidewire lumen 310. The outer tubular member 306 is disposed preferably concentrically around a substantial portion of the inner member 304 to create an inflation lumen 314 therebetween. The balloon 302 is connected at its proximal end to the distal end of the outer tubular member 306 and at its distal end to the dismal end of the transition member 308.

In a preferred embodiment the inner and outer tubular members 304 and 306 are formed of polyethylene (PE) while the balloon 302 and transition member 308 are formed of polyimide. The transition member 308 may be bonded to the inner member 304 by an adhesive such as URETHANE 3507 available from the H. B. Fuller Company of St. Paul, Minn. The balloon 302 may be bonded to the outer and transition tubular members 306 and 308 by an adhesive such as URETHANE 3507 to form a fluid-tight seal. Alternatively the balloon 302 may be secured by making the balloon 302 from heat shrinkable irradiated material.

The dimensions of the catheter are dependent upon the size of the guidewire used in conjunction therewith. For example, in a preferred embodiment using a 0.014 inch guidewire, the transition member 308 has an inner diameter of about 0.018 inches, an outer diameter of about 0.0208 inches and a length of about 1.0 inches. The dimensions of the inner and outer tubular members 304 and 306 may be conventional as is well known by those skilled in the art.

In a preferred embodiment, the heating element is a coil 312 formed from a 0.001 inch diameter silver wire bifilarly wound around the exterior of the transition member 308. The dimensions of the coil 312 are the same as coil 212 previously described with reference to the guidewire anemometer of FIG. 10 and thus need not be described again.

Coil leads 316 which are an extension of coil 312 extend through a portion of the inflation lumen 314 and are joined with shaft leads 318 which are preferably 0.005 inch diameter insulated silver wire. Together the coil 312 and leads 316 preferably have a resistance of about 14 ohms. The shaft leads 318 extend through the inflation lumen 314 to the proximal of the catheter 300. Each shaft lead 318 has a resistance of about 3 ohms. Connected at the proximal end of the catheter is a manifold (not shown) which is well known to those skilled in the art and thus need not be described in detail. Ports in the manifold allow a guidewire (not shown) to be positioned in the guidewire lumen 310 and inflation fluid to be delivered to the inflation lumen 314. In addition, an electrical connector (not shown) is bonded into an inflation lumen port on the manifold to join the shaft leads 318 to the electrical connector. The connector can be joined to port 152 of instrumentation housing 150 by cable 154 thereby connecting the coil 312 with the circuitry of the present invention.

While the balloon 302 and transition member 308 have been described as formed of polyimide, other materials resistant to melting under high temperatures can be used such as TEFLON, KYNAR and nylon for example. Alternatively, the inner member 304 may be formed of polyimide and extended through the balloon 302 to the distal end of the catheter 300 thereby eliminating the transition member 308. The interior of the transition member 308, or inner member 304 if it is formed of polyimide, is preferably coated with TEFLON to allow the guidewire (not shown) to slide back and forth easily in the guidewire lumen 310.

The coil leads 316 and shaft leads 318 are illustrated as extending between the exterior surface of the inner and transition members 304 and 308 and the interior surface of the outer member 306. Alternatively, the coil leads 316 and shaft leads 318 can be extruded into the walls of the inner tubes 304 and 308 or deposited onto the inner and transition members 304 and 308 using thin film technology. The coil 312 could also be fabricated using thin film technology. In addition, the examples described with reference to the guidewire anemometer of FIG. 10 to extend the leads from the coil to the proximal end of the guidewire can be modified for use with reference to the dilation catheter of FIG. 11. While a particular balloon catheter has been described, those skilled in the art will appreciate that other types of catheters may be used in conjunction with a heating element according to the preferred embodiments of the present invention.

The operation of the circuitry 14 in conjunction with the dilation catheter of FIG. 11 will now be described. As previously described, a selection switch 164 may be provided on the front panel of the instrumentation housing 150 to indicate the specific device in which the coil is embodied. The selection switch is activated to indicate that a dilation catheter according to FIG. 11 has been connected to the display and control circuitry 14 of the present invention. As previously described, the value of certain components of the circuitry illustrated in FIGS. 3a–3e are determined by the device 11 in which the heating element is embodied. In particular, the value of capacitor C5 (FIG. 3a) and the bandwidth of low pass filters 72 and 76 change. Unlike the guidewire anemometer of FIG. 10, catheter 300 does not require the same rapid response from circuitry 14. The time constant of feedback integrator 68 therefore is increased to 0.2 seconds by selecting a larger capacitor preferably having a value of 0.22 $\mu$F. In addition, the bandwidth of filters 72 and 76 is decreased to 1 Hertz by using 1 Megohm resistors R17 and R18 and R21 and R22 (FIG. 3c). In the digital embodiment of FIG. 9, switch 164 (or an appropriate entry on keyboard 154) selects software appropriate to the particular device being used.

While the circuitry shown in FIG. 2b is predominantly used to determine the characteristics of flowing fluid, using it with the catheter of FIG. 11 provides useful information concerning the nature of material in contact with the balloon. For example, if the material is fatty, it will act as a heat sink and a greater amount of power will have to be delivered to coil 12 to keep it at the set point temperature.

The catheter of FIG. 11 may be used for various procedures. For example, the catheter 300 can be used to perform dilation of an obstructed artery. To use the catheter in such a manner, it is first positioned in the obstructed artery by conventional procedures known to those skilled in the art. The balloon 302 is then preferably inflated to about one (1) atmosphere. A set point temperature is selected by turning control knob 158 provided on the front panel of instrumentation housing 150. Heat switch 160 is flipped to its heat setting for 30 to 60 seconds. The inflation pressure within the balloon 302 is then increased until the dilation is complete. The heat is then switched off and the balloon is deflated and removed. The heat provided by the coil 312 is transferred to the surface of the balloon 302 through the inflation fluid thereby delivering heat to the arterial wall in contact with the balloon surface. The heat softens plaque on the arterial wall so that dilation may occur at a pressure lower than would otherwise be required. (See U.S. Pat. No. 4,799,479 (Spears)).

Another example of the manner in which the catheter 300 of FIG. 11 can be used is in conjunction with stent delivery and placement. The catheter 300 may be used to deliver and position stents within the vascular system. More specifically, a heat expandable stent (not shown) is positioned over the balloon 302 of the catheter before the balloon is inflated. The balloon and stent are correctly positioned in the vascular system. Heat switch 160 is flipped to its heat setting and current is delivered to the coil 312 to increase its temperature to preferably about 65° C. to about 70° C. for a period of about 1 minute. The balloon 302 is then inflated to a pressure preferably of about six (6) atmospheres which expands the stent into position. The heat switch 160 is then flipped to its standby position to avoid heating the arterial wall.

An advantage of this embodiment of the present invention is that the temperature of the heating element, i.e. coil 312, which is the hottest point on the catheter, is being measured as opposed to measurements made on the balloon surface. By measuring the temperature at the hottest point on the catheter, greater protection is provided to the tissue in contact with the balloon surface.

FIG. 12 illustrates a cross-sectional view of a nonintravascular device in the form of an in-line anemometer usable with the apparatus of FIG. 1 according to a third preferred embodiment. The in-line anemometer 500 includes an inner tube 502, two side tubes 504 and outer tube 506. The heating element is formed by a coil 512 wound around the exterior of the inner tube 502.

In a preferred embodiment, the inner tube 502 is a polyimide tube with an outer diameter of about 0.04 inches and an inner diameter of about 0.038 inches. The side tubes 504 are formed of TEFLON having an inner diameter of about 0.045 inches and an outer diameter of about 0.060 inches. The outer tube 506 is also formed of TEFLON having an inner diameter of about 0.065 inches and an outer diameter of about 0.125 inches. The coil 512 is formed by 150 turns of 0.0012 inch diameter silver wire bifilarly wound about the exterior of the inner tube 502. Preferably the coil 512 is centered on the inner tube 502 as illustrated.

Concentrically placed around the inner tube 502 and abutting the sides of the coil 512 are side tubes 504. Side tubes 504 are bonded to inner tube 502 as illustrated. While exaggerated in the illustration, there is a small annular lumen formed between the exterior of the side tubes 504 and the interior of the outer tube 506. The coil leads 514 emerge through this annular lumen, and this space is otherwise filled with adhesive (not shown). The outer tube 506 is concentrically placed around the coil 512 and a portion of the inner tube 502 and side tubes 504. Preferably the outer tube 506 is centered over the coil 512 as illustrated. Thus the coil 512 is surrounded on three sides by insulating materials such as TEFLON or other insulating tubing with a suitably high melting temperature. A thin walled inner tube 502 preferably having a wall thickness of about 0.001 inches separates the inner coil surface and the flowing liquid.

FIG. 13 illustrates a schematic of the in-line anemometer 500 shown in FIG. 12. In a preferred embodiment, anemometer 500 is used to measure the speed of flowing fluid directed through the inner tube 502. In a particular preferred embodiment, anemometer 500 can be used to measure the volumetric flow rate blood taken out of the body of a patient and diverted through the inner tube 502, and then sent back into the body of a patient for example, in terms of milliliters per minute. The ends of the side tubes 504 shown at 516 and 518 can be connected to inlet and outlet tubes (not shown) transporting blood out of and into the patient.

Leads 514 extend from the coil 512 through the lumen created between the exterior of side tubes 504 and the interior of outer tube 506. Leads 514 of apparatus 500 are connected to the circuitry 14 through port 152 of the instrumentation housing 150. Various ways of connecting the leads 514 may be provided as will be appreciated by those skilled in the art and thus need not be described in detail. Once anemometer 500 is properly positioned and connected to instrumentation housing 150, a set point temperature is selected by turning control knob 158. If a selection switch 164 is provided, it is set to indicate that anemometer 500 is connected to instrumentation housing 150. Preferably a see point temperature is selected which is about 5° C. above the ambient temperature of the fluid flowing through anemometer 500. The heat switch 160 is flipped to its heat setting to deliver current to coil 512. The heat generated by coil 512 is transferred to the interior of inner tube 502 because of the construction of anemometer 500. In particular, the inner tube 502 is formed of a thin-walled polyimide tube and surrounded by TEFLON side tubes 504 and outer tube 506 which act as an insulator. As cooler fluid flows through inner tube 502, the circuitry 14 measures the power delivered to the coil 512 as described with reference to the guidewire anemometer of FIG. 10. Thus the velocity of the flowing fluid can be determined and displayed as previously described.

While the heating element has been described in the preferred embodiments as a coil, the heating element of the preferred embodiments of the present invention is not limited to coil and other elements may be used.

The electronics of FIG. 3 use alternating current to raise the temperature of the heating element. The use of ac current is required for safety concerns when the device is to be used within a body because direct current and low frequency currents can interfere with the body's electrical conduction systems. This precaution is taken even though all lead wires and heating coils are electrically insulated. The in-line anemometer 500 of FIGS. 12 and 13 functions outside of the body, and in many applications d.c. current can be used to raise the temperature of the heating coil 512. When d.c. current is used, the coil 512 can be wound single filar rather than bifilar because coil inductance is not relevant for d.c. currents.

In addition, if the in-line anemometer of FIG. 12 or the guidewire anemometer of FIG. 10 are constructed using a single filar coil, the impedance of the coil at high frequencies will provide a measure of the dielectric and conductive properties of the blood or fluid flowing past the coil.

Figure 14:
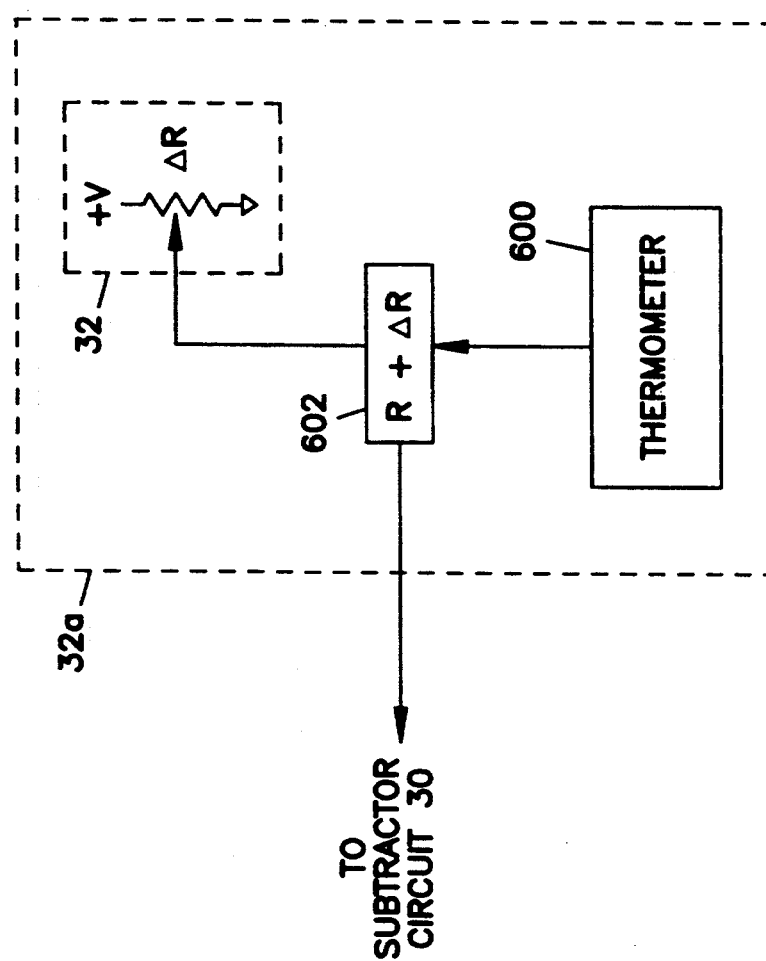
FIG. 14 illustrates a schematic block diagram of a modified set point temperature circuit.

FIG. 14 illustrates a modification to the block schematic of FIG. 1. In particular, the set point temperature circuit 32a has been modified to incorporate an input from an external thermometer 600. The circuitry 14 is modified to address an environment where the temperature of the fluid in which the heating element is placed is either unknown or variable. As described with reference to the in-line anemometer of FIG. 12 and to the guidewire anemometer of FIG. 10, the temperature of the coil 12 is kept a fixed amount higher than the ambient temperature of the fluid. In order to maintain a correct set point temperature in an environment where the temperature of the fluid is either unknown or variable, the output of an external thermometer 600 is converted to an equivalent coil resistance and added to the resistance determined by the set point temperature circuit 32 (FIG. 2a). The addition of a reading from thermometer 600 controls the set point temperature so that the velocity calibration does not change with changing fluid temperature. More particularly, the set point temperature will always be a fixed amount above the ambient temperature of the fluid even when the temperature of the fluid is variable or unknown.

As shown in FIG. 14, an adder circuit 602 receives inputs from set point temperature circuit 32 and from thermometer 600. The thermometer 600 can be placed anywhere in the fluid stream but preferably is placed upstream of the heating element to avoid being exposed to heated fluid. It can also be placed on the proximal part of the guidewire anemometer of FIG. 10 but must be inside the body of the patient.

These two inputs are added in circuit 602 and applied to subtractor circuit 30 as the set point resistance value. Thermometer 600 may be a resistance thermometer, which may be simply a second silver coil, a thermistor, or an integrated circuit thermometer available from Analog Devices. In addition, thermocouples such as those commercially available from Fluke and infrared non-contact thermometer may be used.

While adder circuit 602 has not been illustrated in the detailed circuitry of FIGS. 3a–e, those skilled in the art will appreciate that an adder circuit is readily constructed with an op-amp such as Model No. 704 available from Analog Devices Corporation between the output of buffer 104 and the input to subtractor circuit 30. (see FIG. 2a)

Figure 15A:
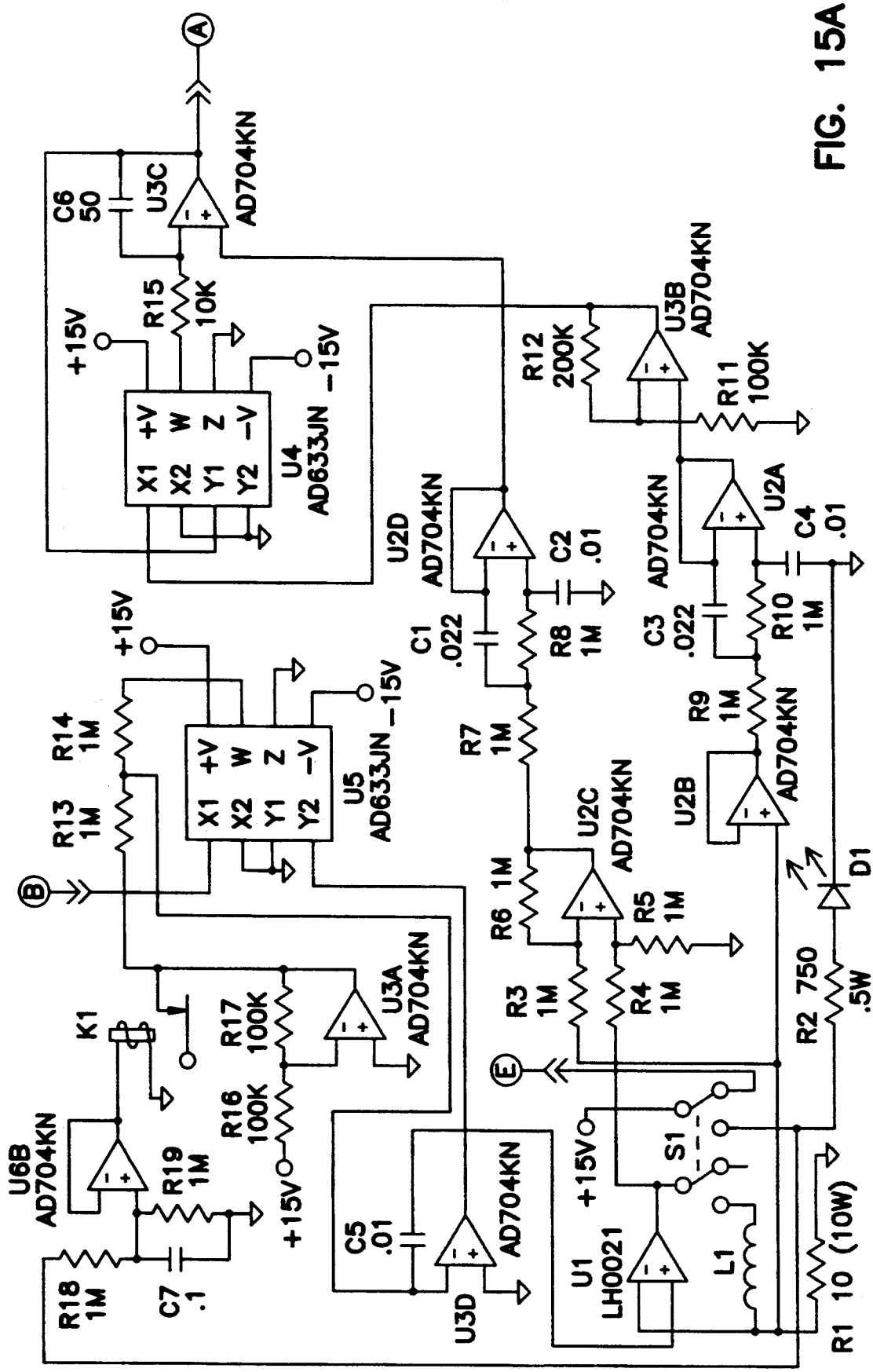
FIG. 15a through 15c illustrate a specific embodiment utilizing a direct current source according to another preferred embodiment of the present invention.
Figure 15B:
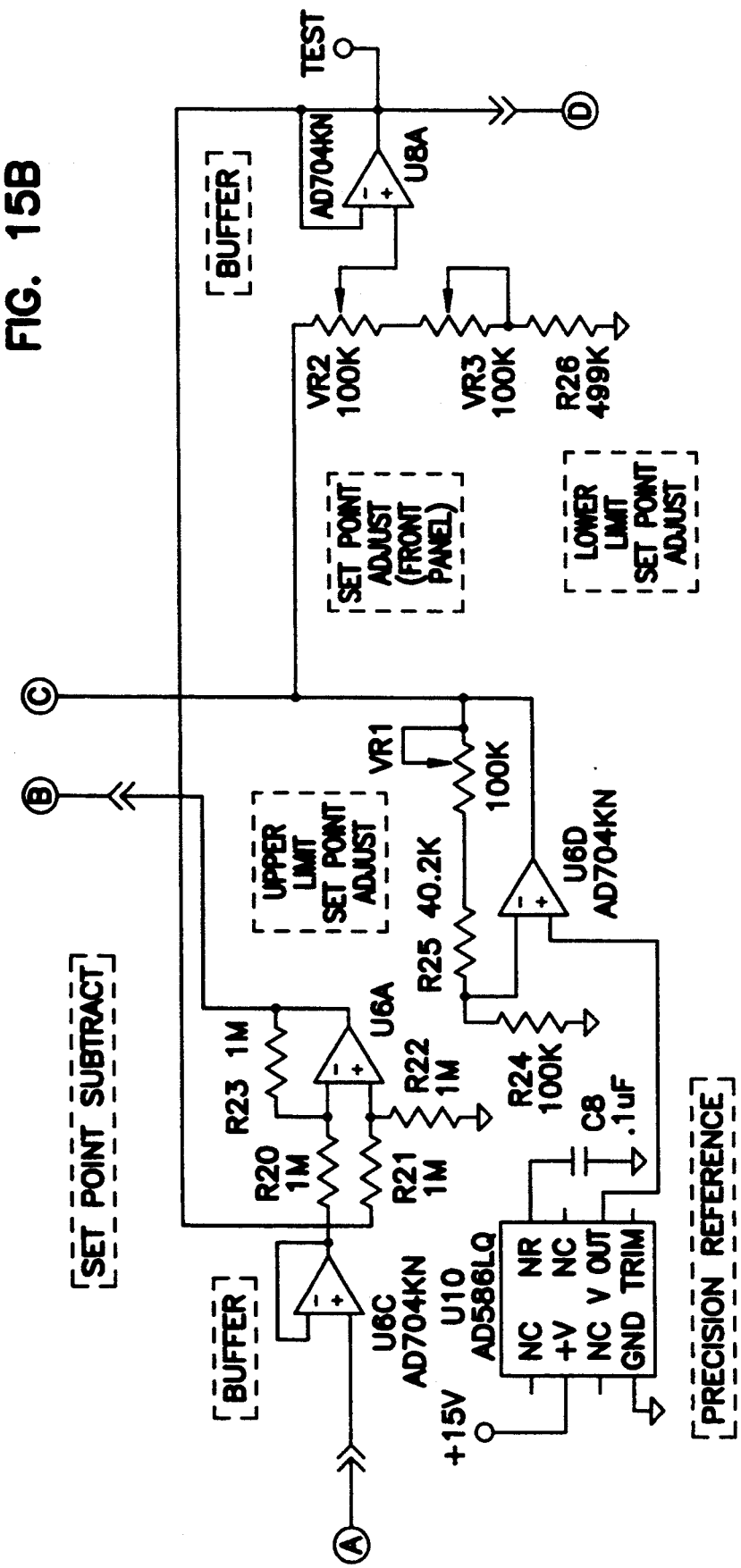
Figure 15C:
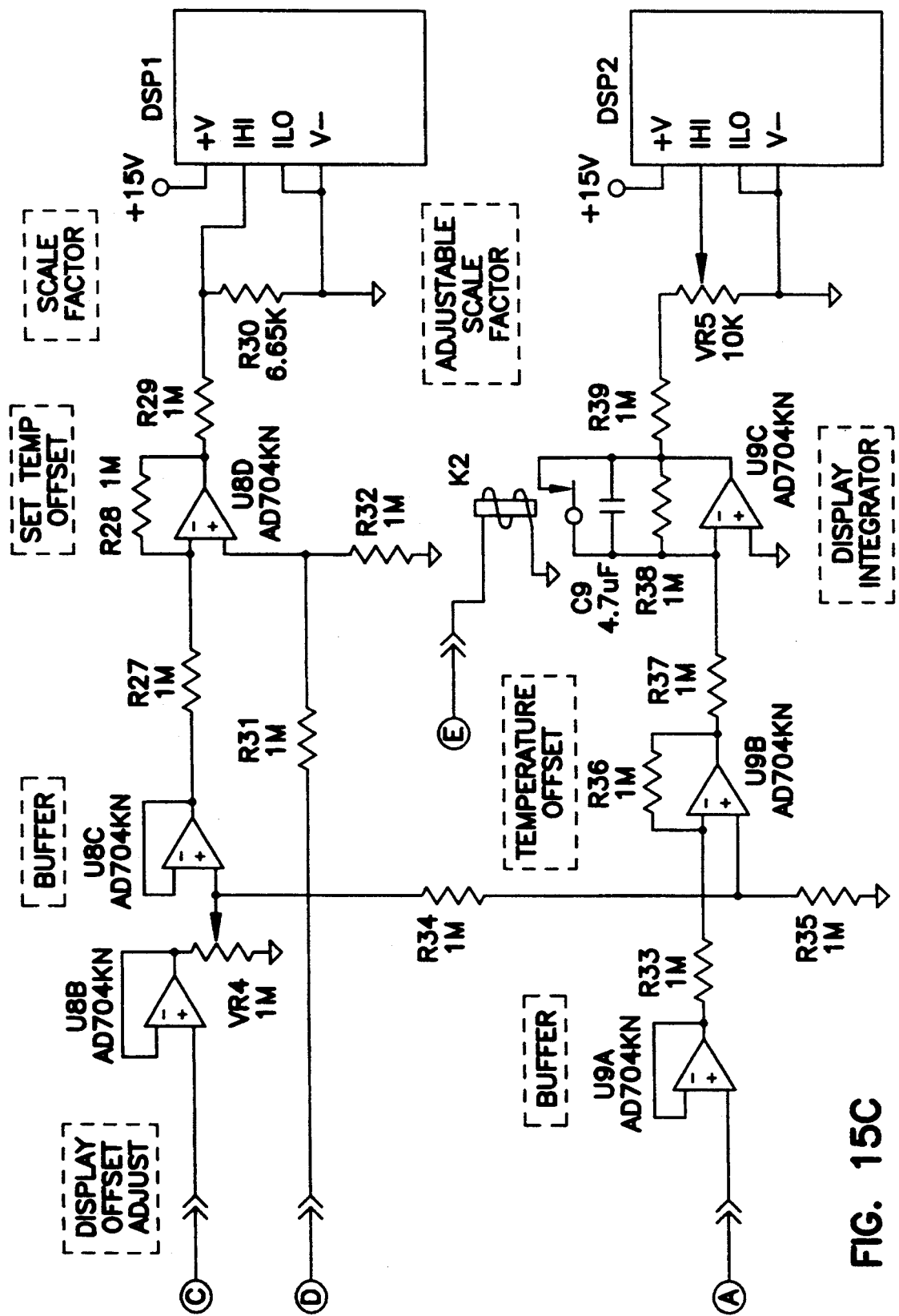

It will be clear to those skilled in the art that the electronics of FIG. 3 can be used to control the temperature of any silver coil which is bifilar wound on an insulating or conducting fixture. For applications outside of the body, the coil may be single filar wound and the electronics can be operated using d.c. current. Examples include thermal bonding of polymer tubes and balloons used in balloon catheters and thermally modifying the shape of polymer tubes used in balloon catheters. FIGS. 15a–c illustrate a specific embodiment of d.c. electronics that may be used in such applications. As previously mentioned, when using a direct current source the r.m.s. to d.c. conversion of the coil current and voltage is eliminated as well as the amplitude controlled oscillator. Also, a less expensive, lower frequency, power op amp model LH0021 available from National Semiconductor of Santa Clara, Calif. may be used.

While the invention has been shown and described in connection with particular preferred embodiments, it is apparent that certain changes and modifications, in addition to those mentioned above, may be made by those who are skilled in the art without departing from the basic features of the present invention. Accordingly, it is the intention of the applicant to protect all variations and modifications within the true spirit and valid scope of the invention.

What is claimed is:

1. An apparatus for performing intravascular therapy comprising:

a catheter having a shaft and a balloon attached to a distal portion of the shaft wherein the interior of the balloon communicates with an inflation lumen in the shaft used to deliver inflation fluid to the interior of the balloon;

a controlled signal source for generating a variable driving signal;

a heating element located in the interior of the balloon, the heating element communicating with the signal source which receives the variable driving signal and heat the inflation fluid within the balloon;

a current meter communicating with the heating element which measures the current flowing through the heating element;

a voltage meter communicating with the heating element to measure the voltage across the heating element;

a divider circuit communicating with the current meter and the voltage meter which generates a measured signal;

a subtractor circuit communicating with the measure signal which compares the measured signal with a desired signal and generates an output signal representative of the comparison; and a feedback circuit communicating with the subtractor circuit to receive the output of the subtractor circuit and generate an output signal having an exponential relation to the output of the subtractor circuit, the output of the feedback circuit communicating with the signal source to vary the driving signal delivered to the heating element;

wherein the shaft of the catheter includes an inner tubular member extending through the interior of the balloon, an outer tubular member concentrically located around the exterior of the inner tubular member wherein the inflation lumen is formed between the outer and inner tubular members, wherein the heating element is supported on the inner tubular member.

2. An apparatus according to claim 1 wherein the heating element comprises a coil bifilarly wound around the inner tubular member.

3. An apparatus according to claim 2 wherein the coil is formed from a silver wire.

4. An intravascular anemometer comprising:
a guidewire having a proximal and distal end; and
a heating element located near the distal end of the guidewire wherein the temperature of the heating element is directly proportional to the resistance of said heating element and said heating element is raised to a selected target temperature and the power needed to maintain the temperature of the heating element at said selected target temperature when the guidewire is positioned in the vasculature is measured and converted into a velocity measurement and wherein the resistance of said heating element is measured and used to modulate the power provided to said heating element to maintain said heating element at said selected target temperature during said velocity measurement.

5. An anemometer according to claim 4 wherein the guidewire includes:
a guidewire core having a proximal and distal end; and
a tubular member positioned over a distal portion of the guidewire core, the tubular member connected to the guidewire core at a position distal from the proximal end of the guidewire core, wherein the heating element is located on the tubular member.

6. An anemometer according to claim 5 wherein the heating element comprises a coil bifilarly wound around an exterior portion of the tubular member.

7. An in-line anemometer comprising:
an inner tubular member defining an inner lumen;
a heating element positioned on the exterior of the inner member;
an intermediate member formed by two side tubes, each tube placed concentrically over an end portion of the inner tubular member wherein the tubes are separated from one another by the heating element; and
an outer tubular member concentrically disposed over the heating element and a portion of the side tubes, wherein the temperature of the heating element is raised to a select temperature and the power needed to maintain the temperature of the heating element at the select temperature when fluid is flowing through the inner lumen is measured and the flow rate of the fluid through the tube is derived from said measurement.

8. An in-line anemometer according to claim 7 wherein the inner member is formed of polyimide.

9. An in-line anemometer according to claim 7 wherein the intermediate member and outer member are formed of a low friction material.

10. An in-line anemometer according to claim 7 wherein the heating element is a coil wound around the exterior of the inner member.

11. An in-line anemometer comprising:
an inner member having an inner lumen, and said inner lumen having an exterior surface; a heating element being placed on said exterior surface of the inner member;
an intermediate member formed by two side tubes, each tube placed concentrically over a portion of the inner member, the two side tubes being separated by the heating element;
an outer member concentrically disposed over the combination of the inner member, heating element and intermediate member;
a controlled signal source means for generating a variable driving signal wherein the signal source communicates with the heating element and supplies the variable driving signal to the heating element;
a current meter communicating with the heating element which measures the current flowing through the heating element;
a voltage meter communicating with the heating element to measure the voltage across the heating element;
a divider circuit communicating with the current meter and the voltage meter which generates a measured signal; and
a subtractor communicating with the measured signal which compares the measured signal with a desired signal and generates an output signal representative of the comparison, the output of the subtractor communicating with the signal source to vary the driving current delivered to the heating element.

12. An anemometer for measuring blood flow in a vascular comprising:
an elongate body structure for introduction into said vasculature, and having a proximal end and having a distal end;
a heating element located proximate to said distal end of said body structure and exposed to blood flow in said vasculature;
said heating element exhibiting a resistance proportional to the temperature of said heating element, and said heating element coupled to a modulated current source;
means for establishing a target temperature for said heating element;
a linear feedback control system for modulating said modulated current source when said heating element is near a selected target temperature range defined with respect to said target temperature;
a non-linear feedback control system for modulating said modulated current source when said heating element is outside of a selected target temperature range defined with respect to said target temperature;
whereby, said temperature of said heating element is maintained at said target temperature for determination of blood velocity at the location of said heating element.

13. The apparatus of claim 12 wherein said elongate body structure comprises a guidewire having an exterior surface, with said heating element located on said exterior surface.

14. The apparatus of claim 12 wherein said elongate body structure comprises a catheter having an exterior surface and an interior lumen, with said heating element located on said exterior surface.

15. The apparatus of claim 12 wherein said elongate body structure comprises a catheter having an exterior surface and an interior lumen, with said heating element located on said interior lumen.

* * * * *

UNITED STATES PATENT AND TRADEMARK OFFICE
CERTIFICATE OF CORRECTION

PATENT NO. : 5,346,508

DATED : September 13, 1994

INVENTOR(S) : Roger Hastings

It is certified that error appears in the above-identified patent and that said Letters Patent is hereby corrected as shown below:

In column 4, line 31, please delete the word "inventions", and insert therefor --invention--

In column 6, line 53, please delete the word "see", and insert therefor --set--

In column 7, line 19, please delete "d.c.", and insert therefor --dc--

In column 8, line 3, please delete the word "no", and insert therefor --to--

In column 8, line 37, after the word "shown", please insert the word --in--

In column 9, lines 36 and 39, please delete "r.m.s.", and insert therefor --rms--

In column 12, line 36, please delete the word "inputted" and insert therefor --input--

In column 14, line 53, please delete the word "nitinol" and insert therefor --NITINOL--

In column 14, line 63, after the word "having", please delete "an", and insert therefor --a--

UNITED STATES PATENT AND TRADEMARK OFFICE
CERTIFICATE OF CORRECTION

PATENT NO. : 5,346,508

DATED : September 13, 1994

INVENTOR(S) : Roger Hastings

It is certified that error appears in the above-identified patent and that said Letters Patent is hereby corrected as shown below:

In column 16, lines 17 and 40, please delete "d.c.", and insert therefor --dc--

In column 17, line 51, please delete the word "dismal", and insert therefor --distal--

In column 18, line 35, please delete the word "nylon", and insert therefor --NYLON--

In column 20, line 63, please delete the word "see", and insert therefor --set--

In column 21, lines 24, 25, and 28, please delete "d.c.", and insert therefor --dc--

In column 22, lines 18, 23, and 25, please delete "d.c.", and insert therefor --dc--

In column 22, line 25, please delete "r.m.s.", and insert therefor --rms--

In column 23, line 68, please delete the word "polyimide", and insert therefor --polyamide--

In column 24, line 41, please delete the word "vascular", and insert therefor --vasculature--

Signed and Sealed this

Twenty-sixth Day of March, 1996

*Attest:*

BRUCE LEHMAN

*Attesting Officer*     *Commissioner of Patents and Trademarks*